(12) United States Patent
Bayachou et al.

(10) Patent No.: US 7,914,664 B2
(45) Date of Patent: Mar. 29, 2011

(54) NITRIC OXIDE SENSOR

(75) Inventors: Mekki Bayachou, Copley, OH (US); Pubudu Peiris, Cleveland, OH (US)

(73) Assignee: Cleveland State University, Cleveland, OH (US)

( * ) Notice: Subject to any disclaimer, the term of this patent is extended or adjusted under 35 U.S.C. 154(b) by 611 days.

(21) Appl. No.: 11/877,454

(22) Filed: Oct. 23, 2007

(65) Prior Publication Data

US 2008/0223734 A1    Sep. 18, 2008

Related U.S. Application Data

(60) Provisional application No. 60/853,603, filed on Oct. 23, 2006.

(51) Int. Cl.
*G01N 27/26* (2006.01)
*C25B 11/00* (2006.01)

(52) U.S. Cl. .................. 205/781; 204/290.08; 204/431; 204/410; 204/421; 204/429; 73/23.2

(58) Field of Classification Search .......... 204/280–296, 204/410, 411, 421–429; 73/19.01–31.07; 252/500, 514; 257/414, 427, 423
See application file for complete search history.

(56) References Cited

U.S. PATENT DOCUMENTS

| | | | |
|---|---|---|---|
| 5,434,085 | A | 7/1995 | Capomacchia et al. |
| 5,565,075 | A * | 10/1996 | Davis et al. .................. 204/412 |
| 6,280,604 | B1 * | 8/2001 | Allen et al. ................ 205/777.5 |
| 6,287,452 | B1 * | 9/2001 | Allen et al. ................ 205/777.5 |
| 6,649,138 | B2 | 11/2003 | Adams et al. |
| 6,893,552 | B1 | 5/2005 | Wang et al. |
| 7,025,734 | B1 | 4/2006 | Ellis et al. |
| 2003/0031917 | A1 | 2/2003 | Katori et al. |
| 2005/0096519 | A1 | 5/2005 | DeNuzzio et al. |
| 2005/0193800 | A1 * | 9/2005 | DeBoer et al. ................. 73/1.06 |
| 2007/0048181 | A1 * | 3/2007 | Chang et al. .................... 422/57 |
| 2007/0187239 | A1 * | 8/2007 | Weiller et al. ................. 204/424 |
| 2008/0048153 | A1 * | 2/2008 | Naoi ............................. 252/506 |

FOREIGN PATENT DOCUMENTS

WO    WO2005/121022    * 12/2005

OTHER PUBLICATIONS

Zen et al. (Analyst, 2000, 125, 2169-2172).*
J.H. Jang et al. (Journal of Power Sources 123 (2003) 79-85).*
International Search Report (Form PCT/ISA/210).

* cited by examiner

*Primary Examiner* — Alexa D Neckel
*Assistant Examiner* — Jennifer Dieterle
(74) *Attorney, Agent, or Firm* — Fay Sharpe LLP

(57) ABSTRACT

Electrodes comprising ruthenium oxide nanoparticles are disclosed. The ruthenium oxide nanoparticles are located within the electrode or as a coating thereon. The electrode is especially suited for measuring the presence and/or concentration of nitric oxide in a sample.

6 Claims, 34 Drawing Sheets

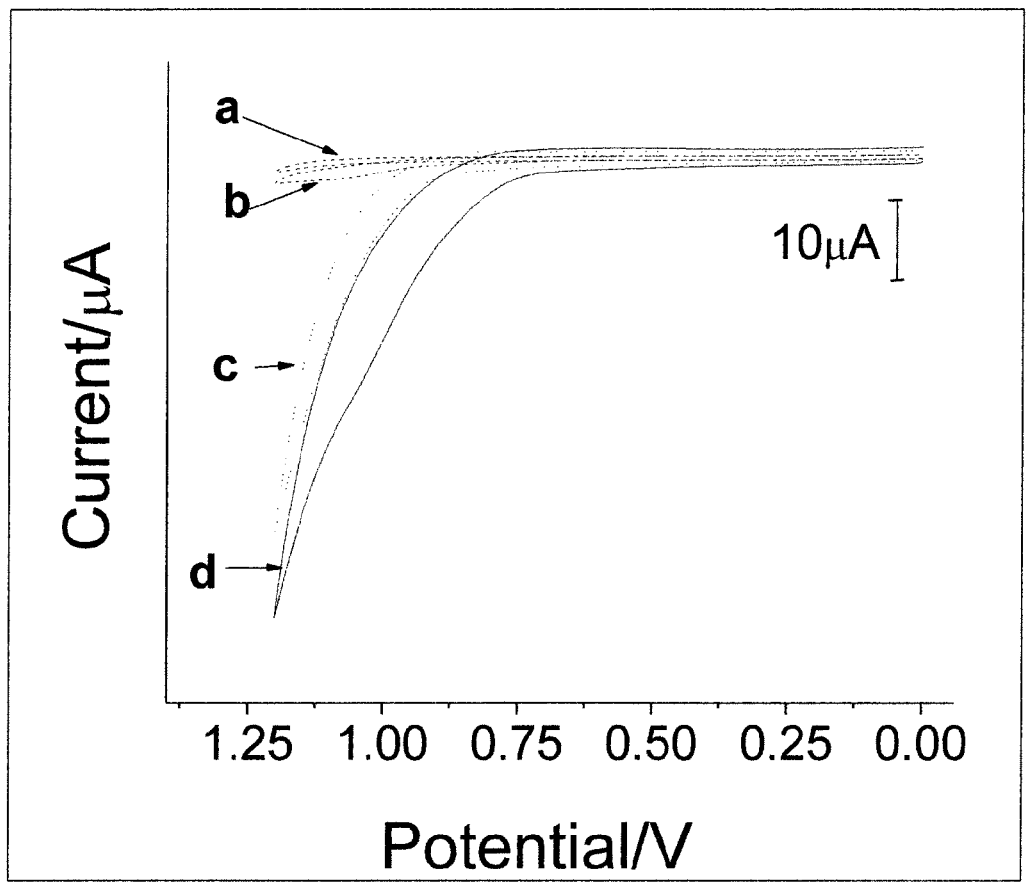
Fig. 1. Cyclic Voltammograms of unmodified (a,b) and modified (c,d) CPEs in the absence (a,c) and presence (b,d) of 4μM NO.

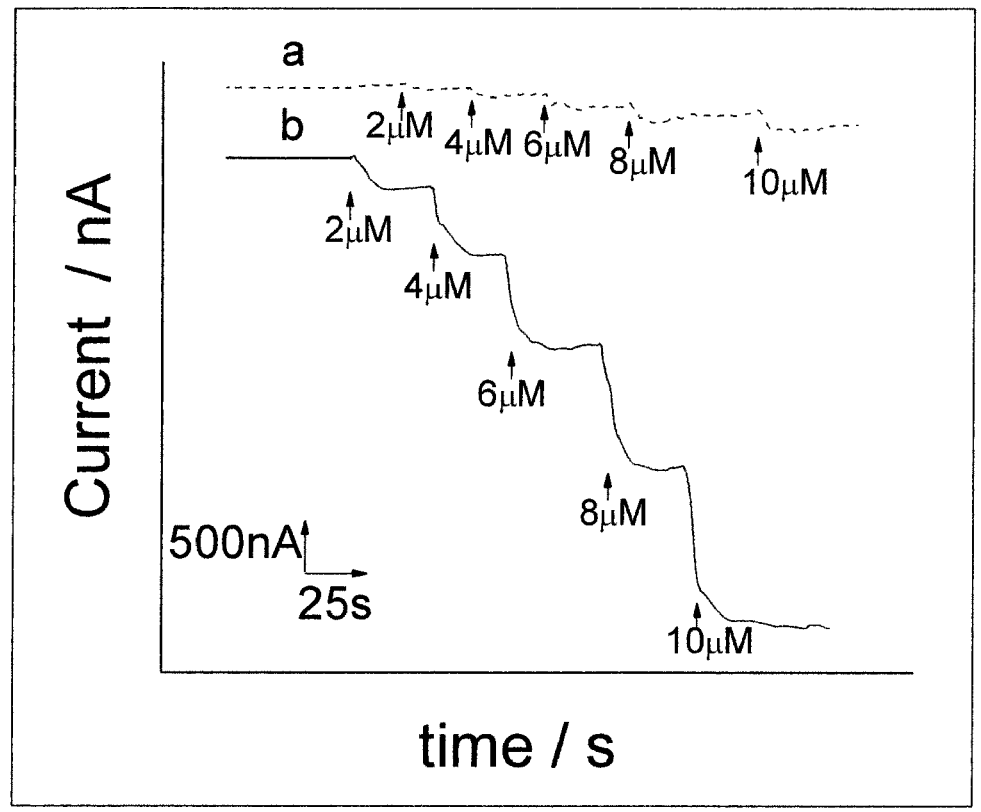
FIG. 3A Amperometric responses of unmodified (a) and $RuO_2$ modified (b) electrodes to NO additions at +0.8V vs. Ag/AgCl.

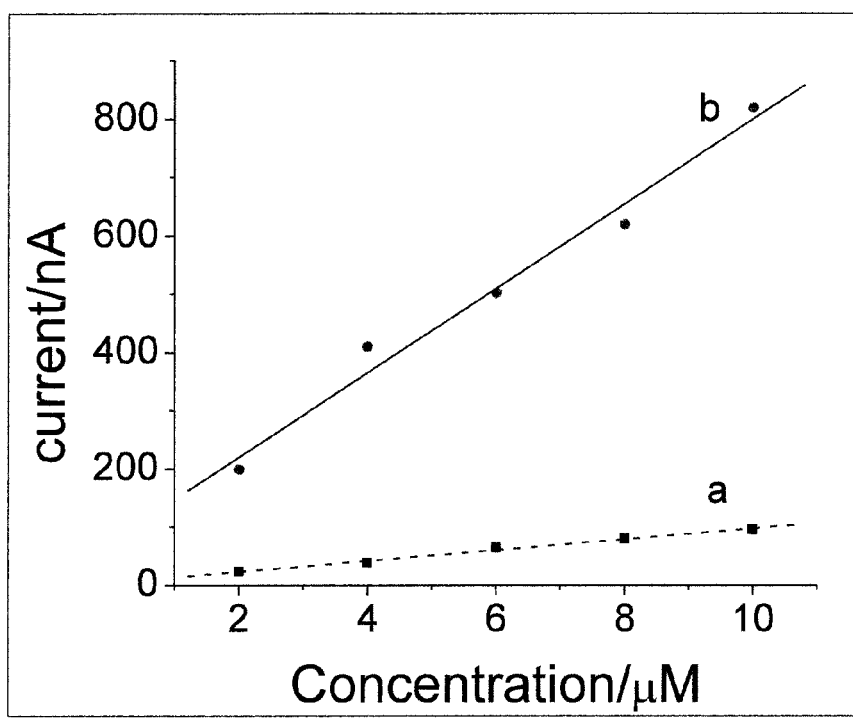
FIG. 3B: Calibration plots based on amperometric responses of modified and non-modified electrodes

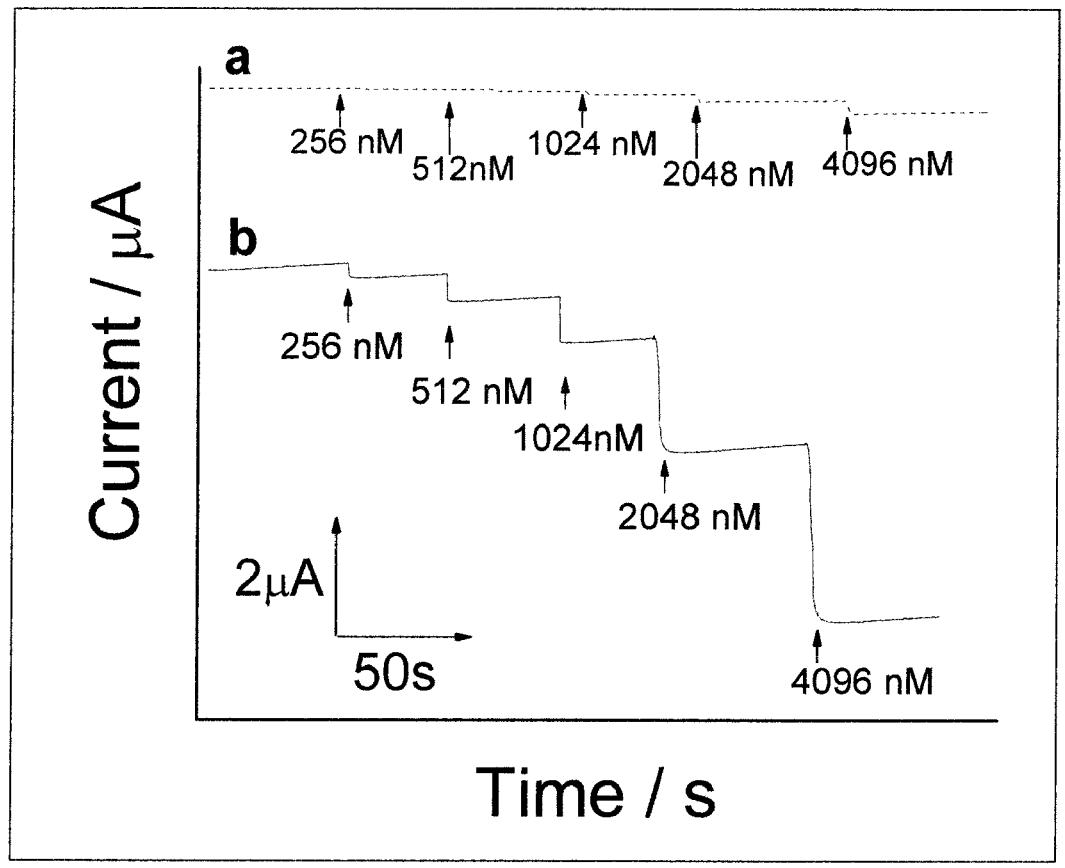
FIG. 4A. Amperomtry of unmodified (a) and RuO$_2$-modified (b) rotating disc CPEs to NO additions (+0.8V vs. Ag/AgCl).

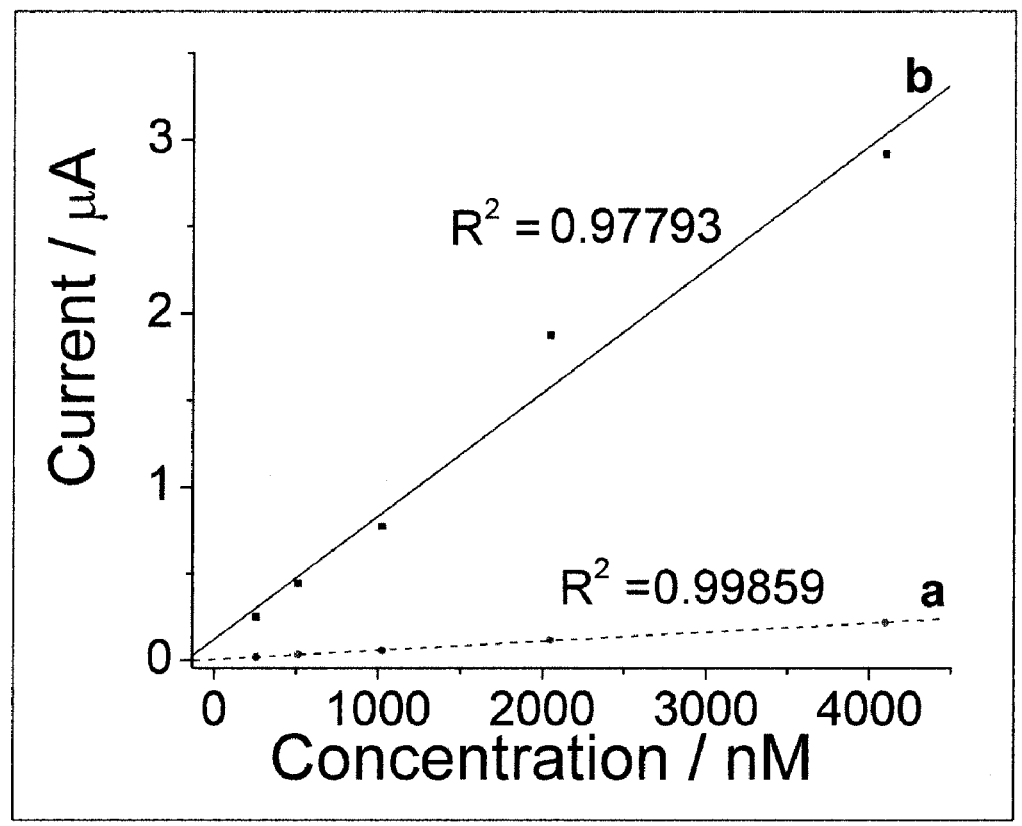
FIG. 4B. Calibration Plots from Fig 4A.

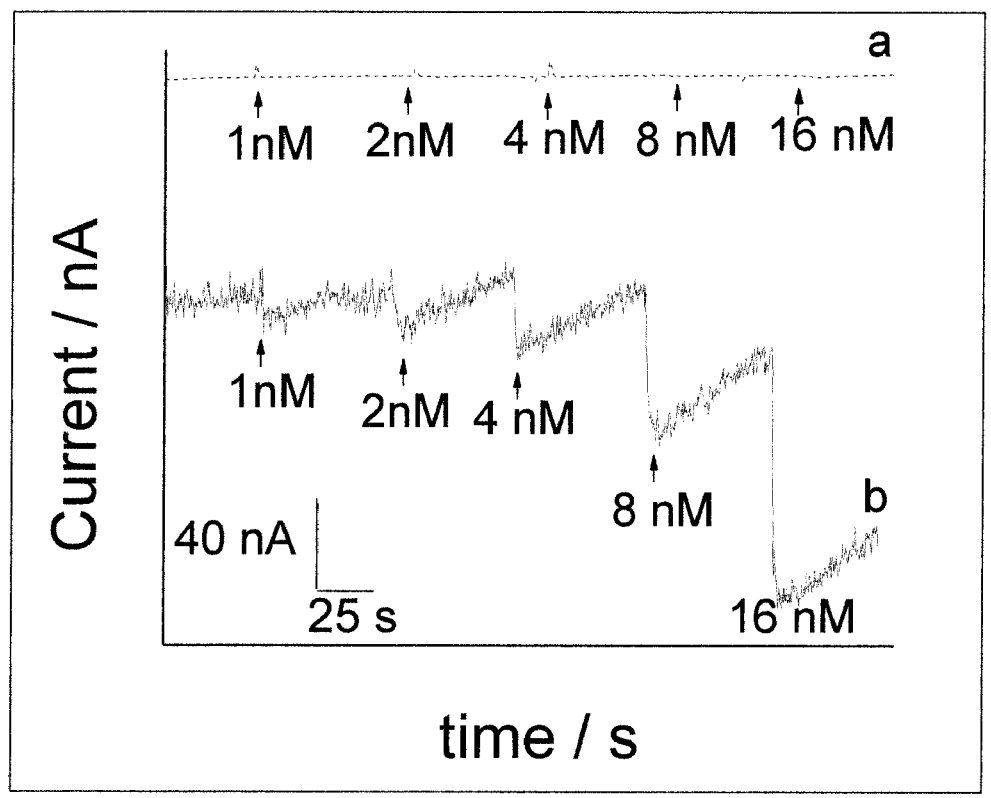
FIG. 5A. Amperometric responses of unmodified (a) and $RuO_2$-modified (b) rotating disc CPEs with successive additions to low nM aliquots of NO at +0.8 vs. Ag/AgCl.

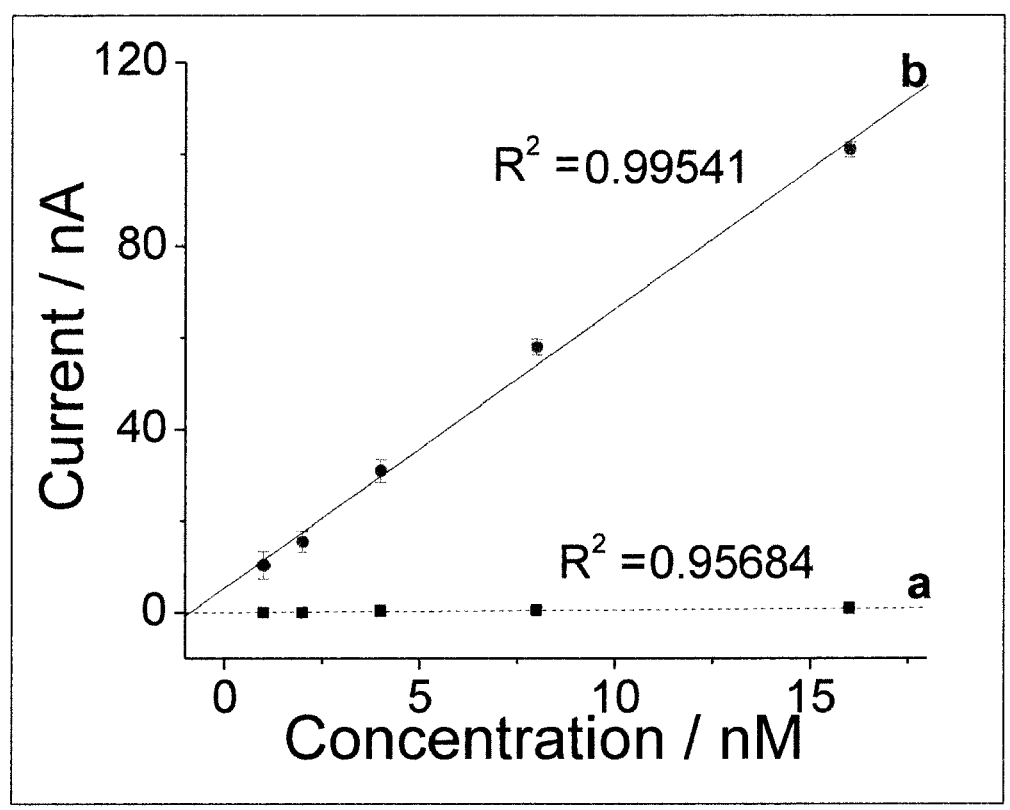
FIG. 5B. Calibration curves based on Fig. 5A

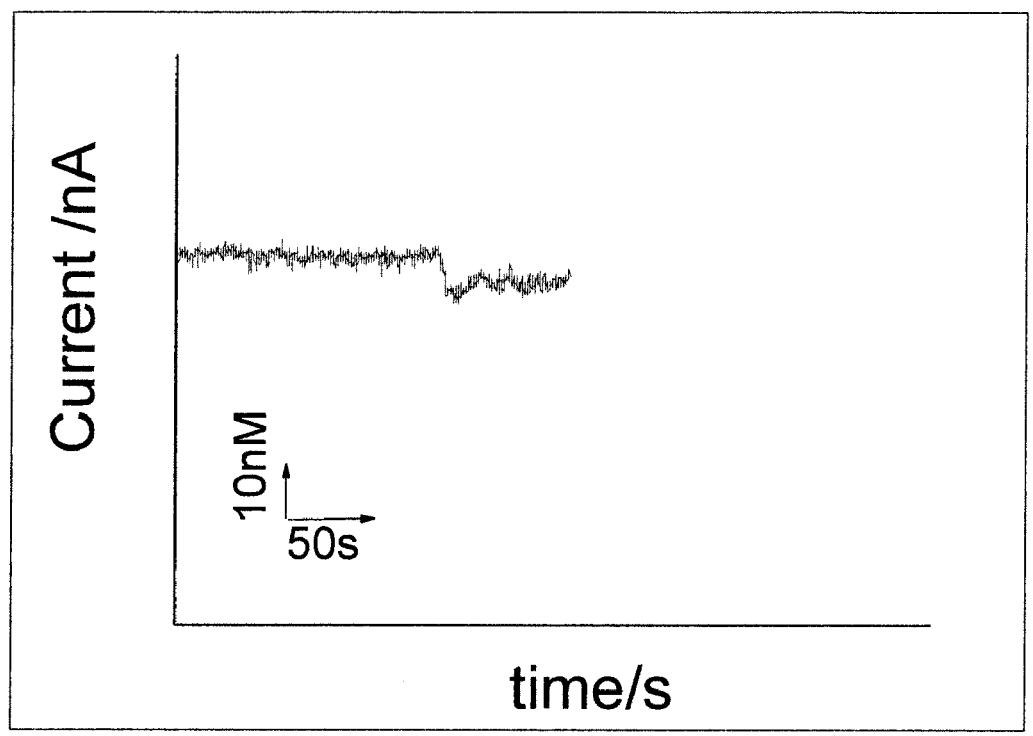
FIG. 6. Typical detection limit of RuO$_2$-modified sensor at 100 pM NO.

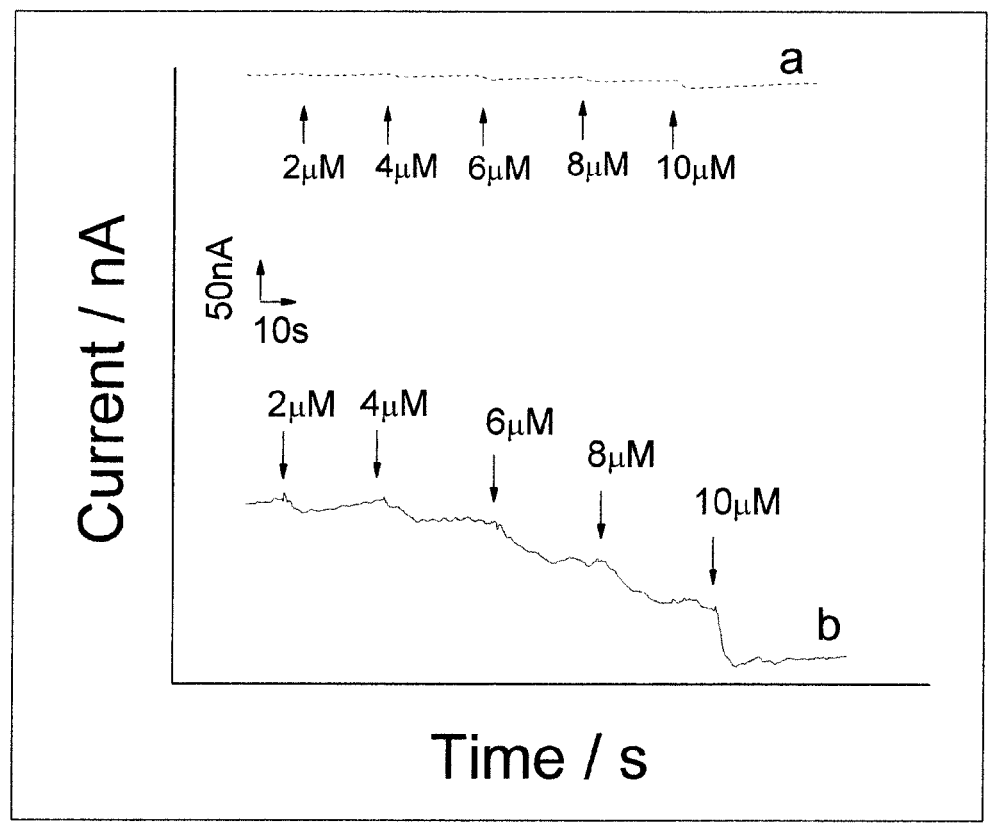
FIG. 7A. Amperometric responses of unmodified (a) and RuO₂-modified (b) CPEs to NO additions at lower applied potential of +0.5 V VS Ag/AgCl.

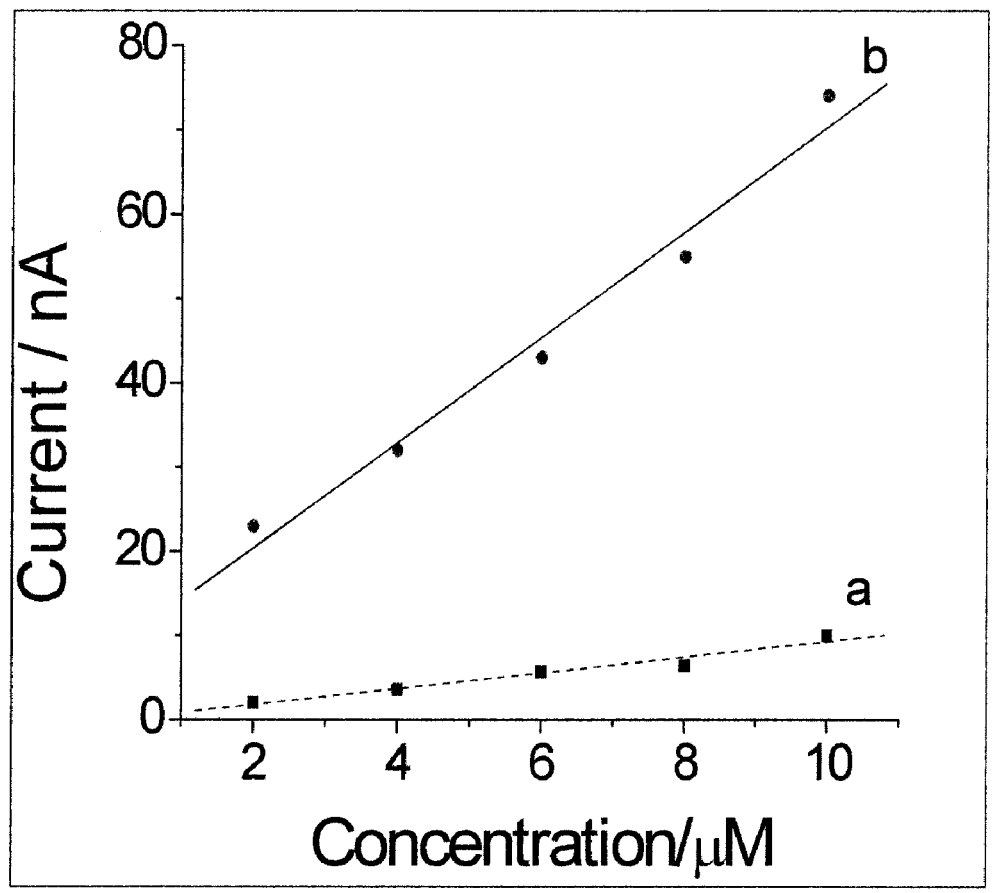
FIG. 7B. The resulting calibration plots based on Fig. 7A.

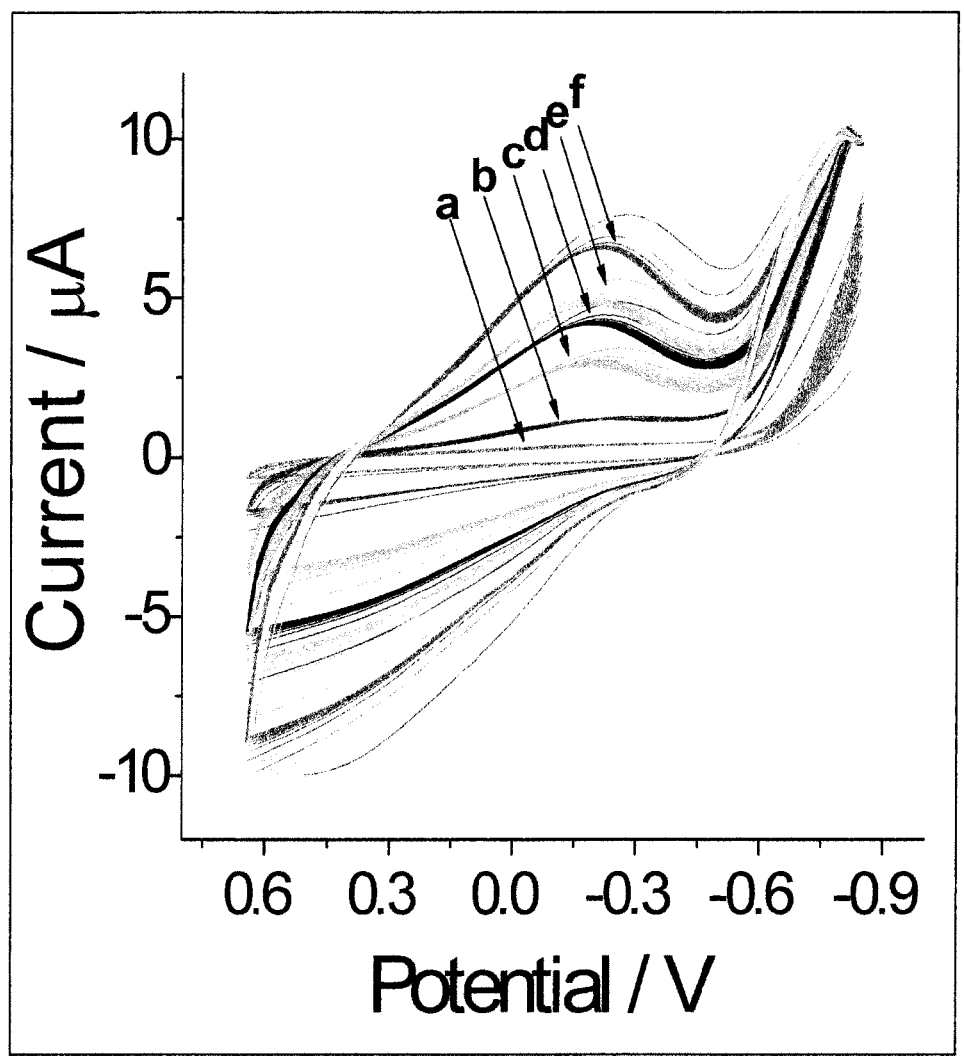
FIG. 8. Series of cyclic voltammograms obtained during RuO2 catalyst electrodeposition on a 7μm sensor.

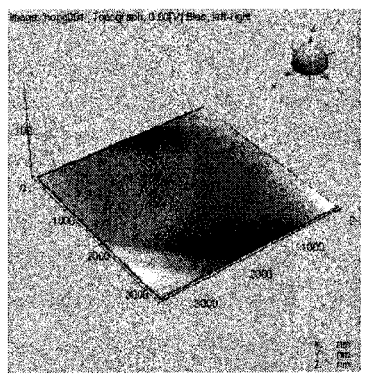
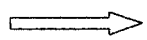
Electrodeposition of ruthenium oxide
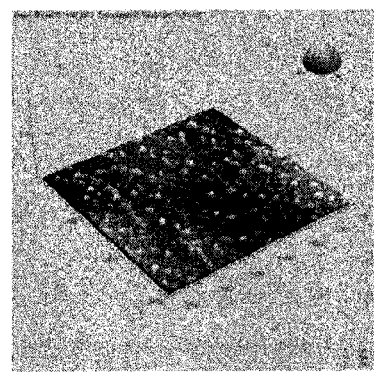
FIG. 11A
FIG. 11B
FIG. 11. Atomic force Microscopy images of bar HOPG (Fig 11A) and RuO2-modified (Fig. 11B) HOPG.

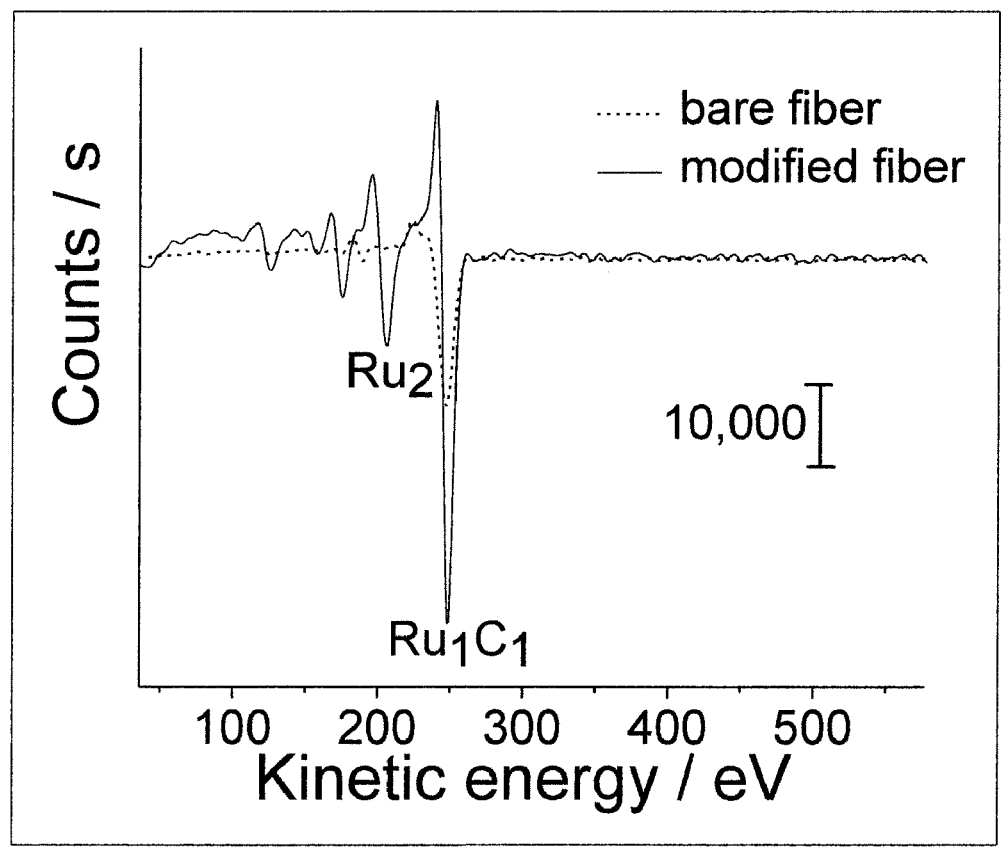
FIG. 13. Auger electron spectra of bare and ruthenium oxide modified 7-μm carbon fibers.

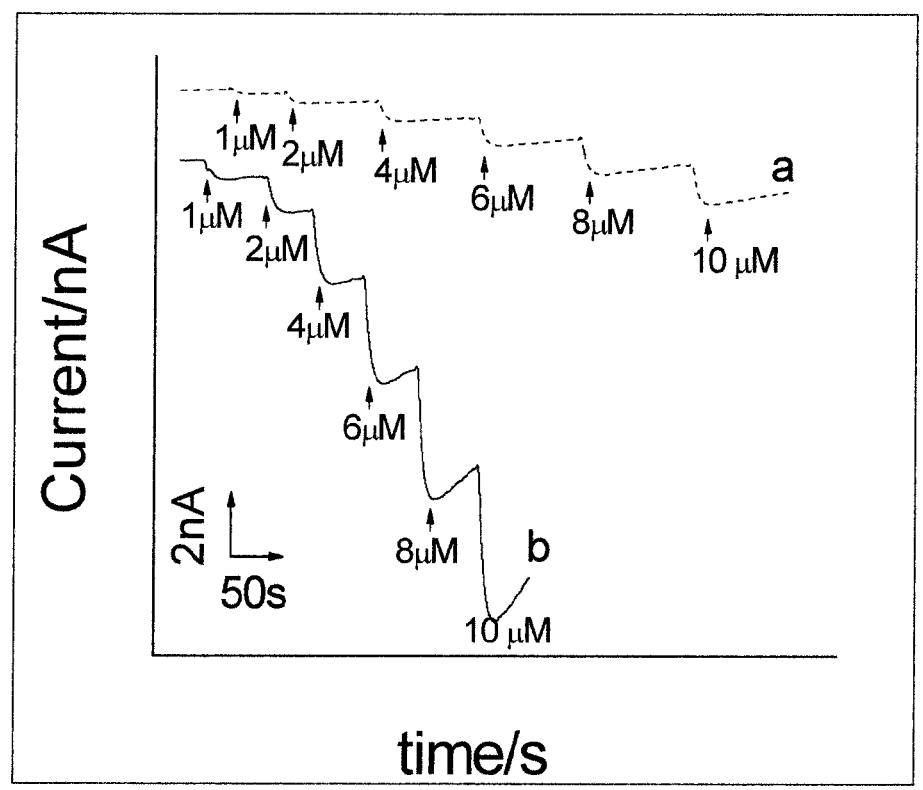
FIG. 14A. Amperometric responses of 7-μm bare (a) and RuO2-modified (b) CFEs to high μM aliquots of NO at +0.8V vs Ag/AgCl.

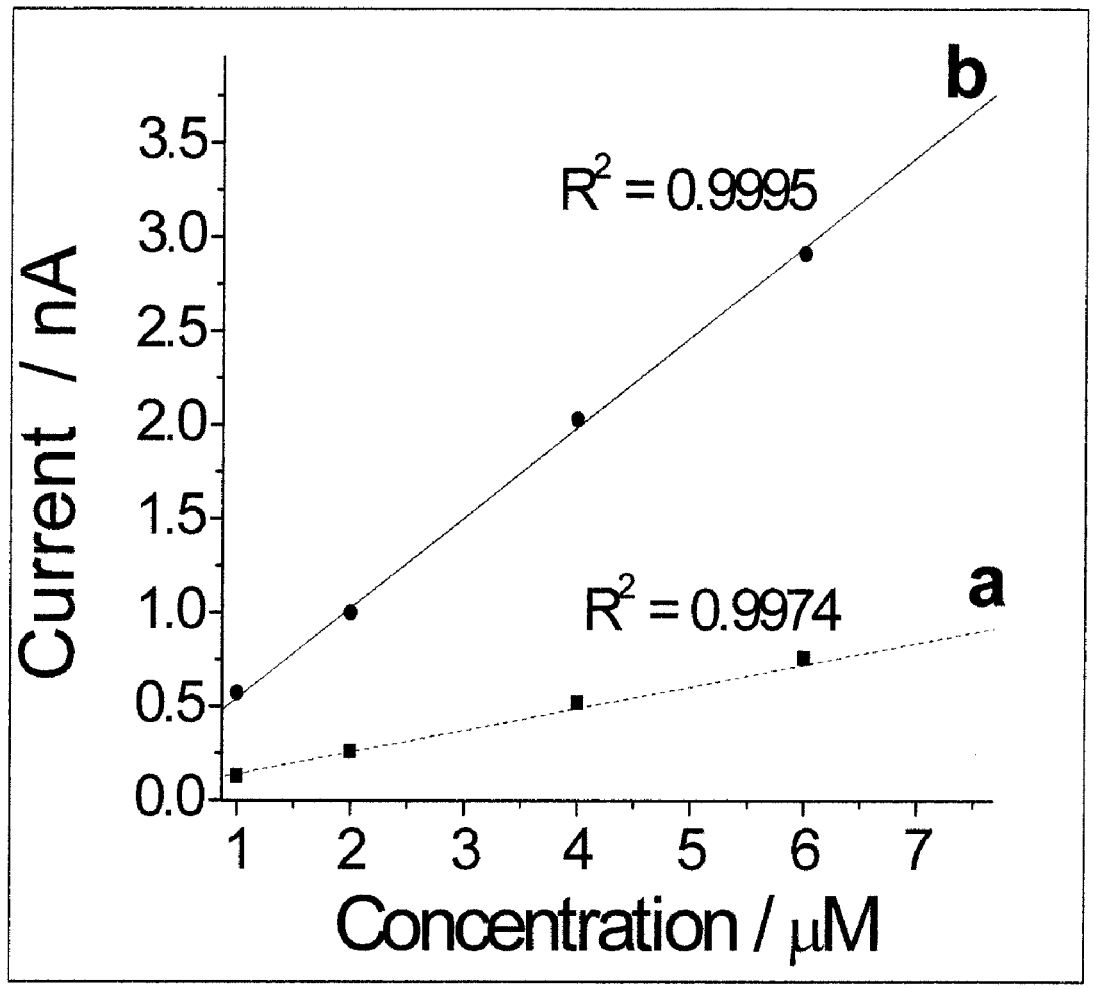
FIG. 14B. Calibration plot from FIG. 14A

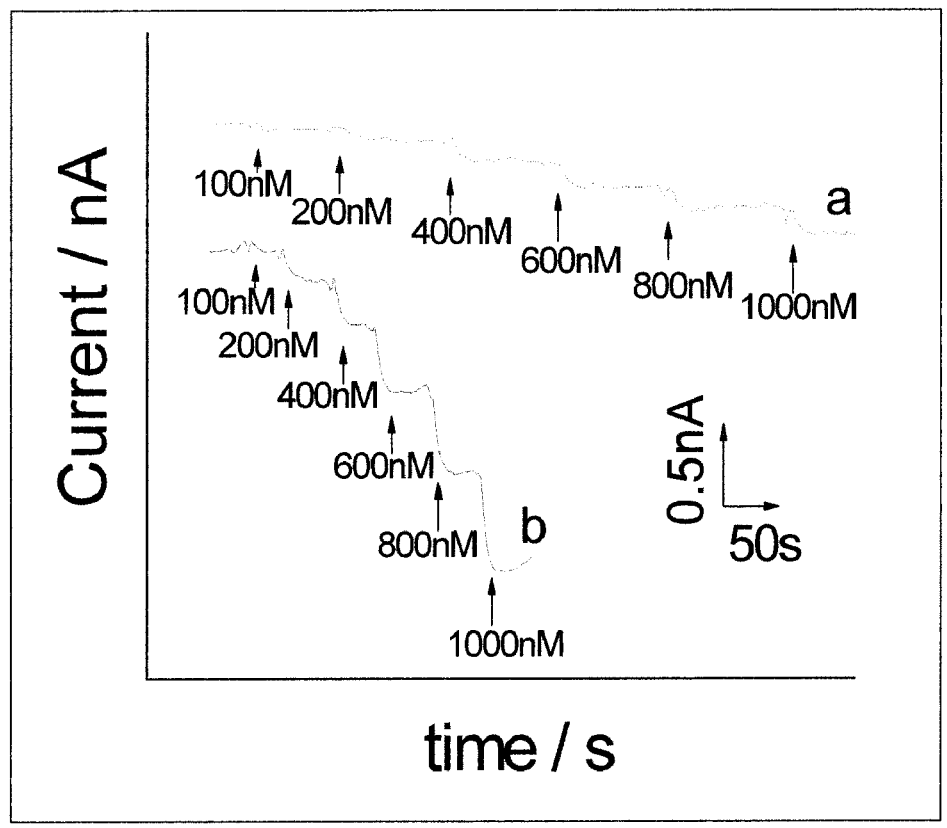
FIG. 14C. Amperometric responses of 7-μm bare (a) and ruthenium oxides modified (b) CFEs in the nanomolar concentration range at 0.8V vs. Ag/AgCl.

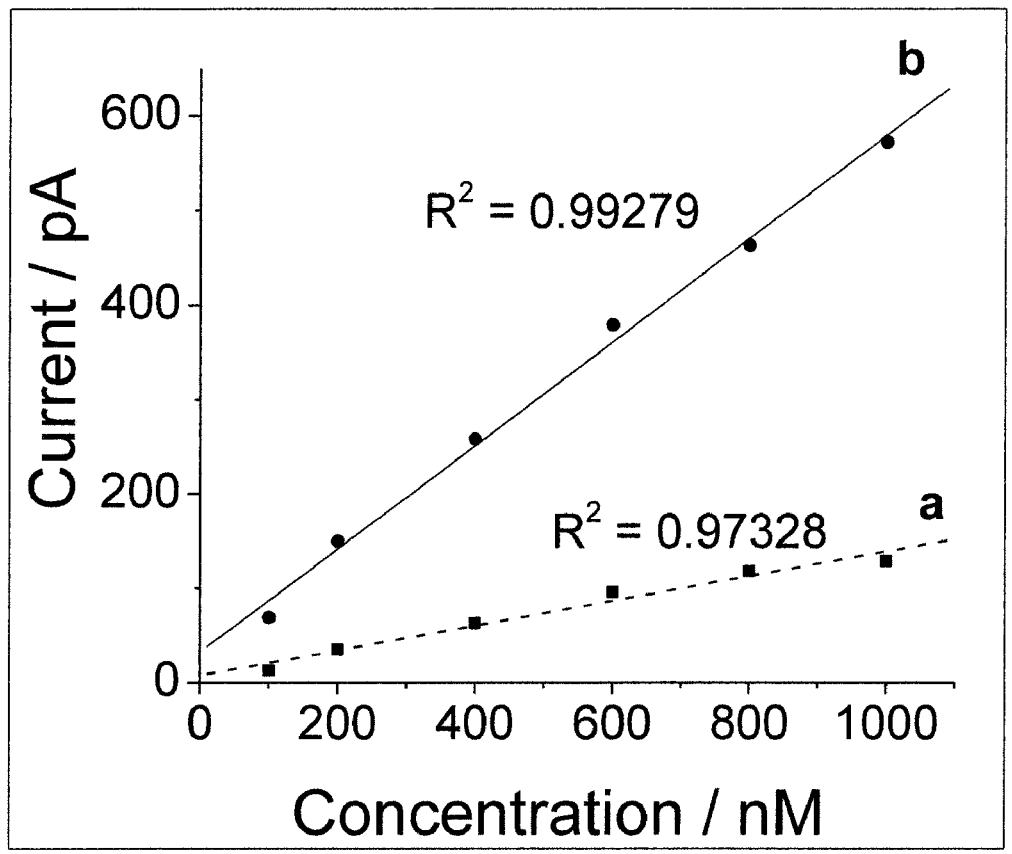
FIG. 14D. Resulting calibration plot from FIG. 14C.

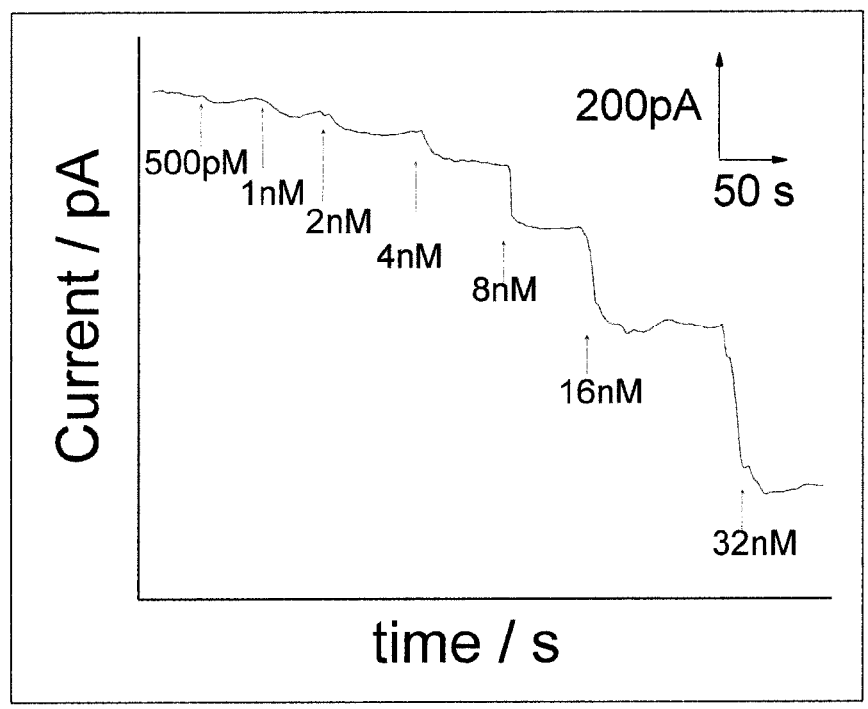
FIG. 15A. Amperometric responses of RuO$_2$-modified CFEs with successive additions of low nM aliquots of NO at +0.8V vs. Ag/AgCl.

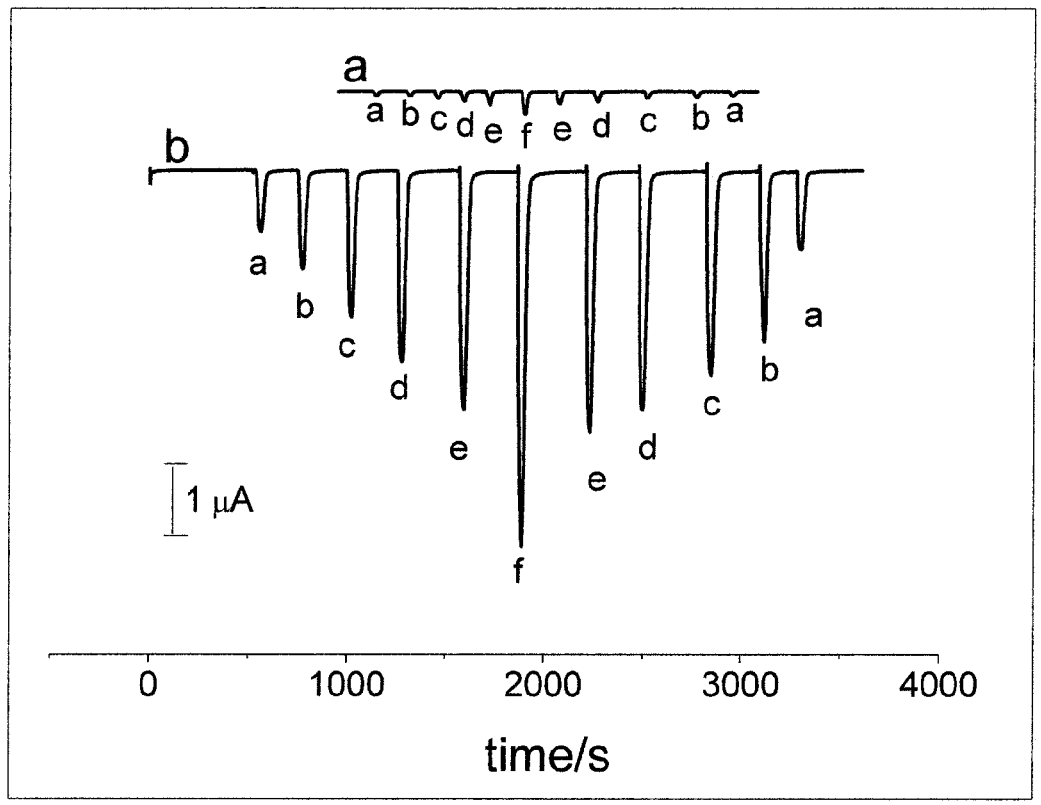
FIG. 16A. Amperometric flow injection analysis responses of unmodified (a) and RuO2-modified (b) 30-μm diameter CFEs with high nM aliquots of NO at +0.8V vs. Ag/AgCl.

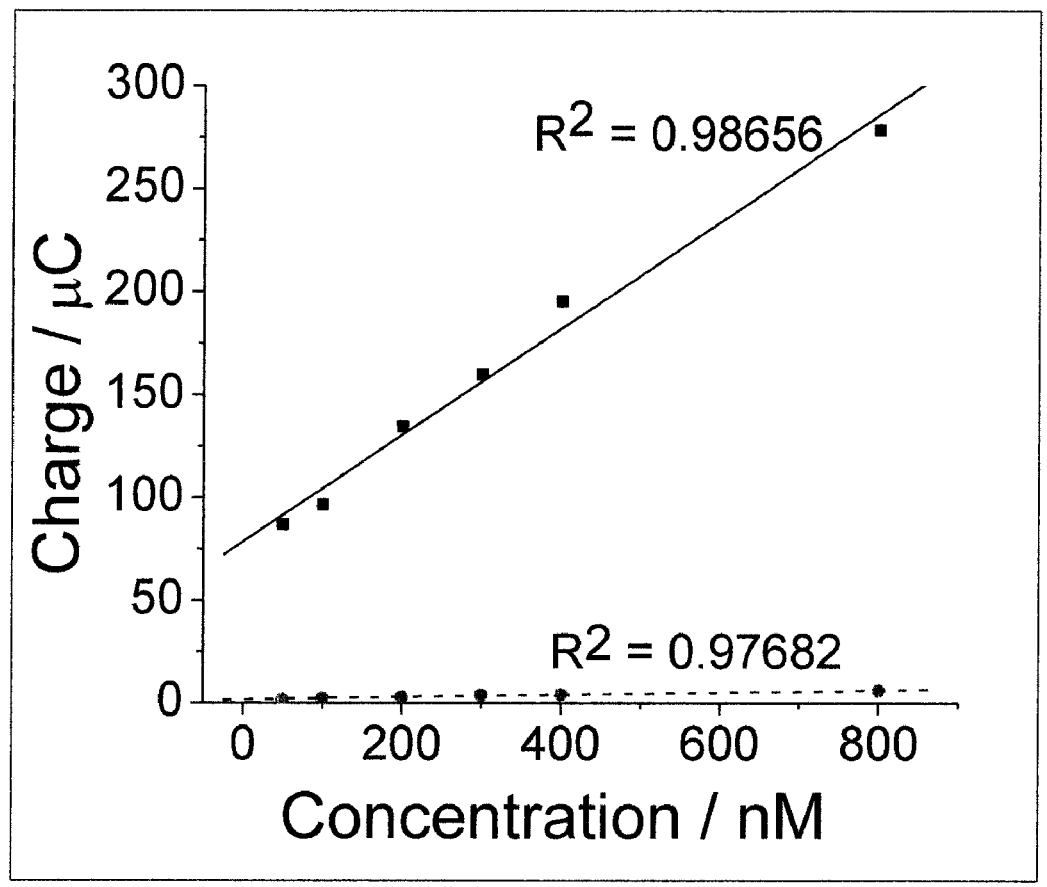
FIG. 16B. The resulting calibration plots based on FIG. 16A

FIG. 17. SEM images of bare (17A and 17B) and RuO2-modified (17C and 17D) 10-μm Pt with magnifications.

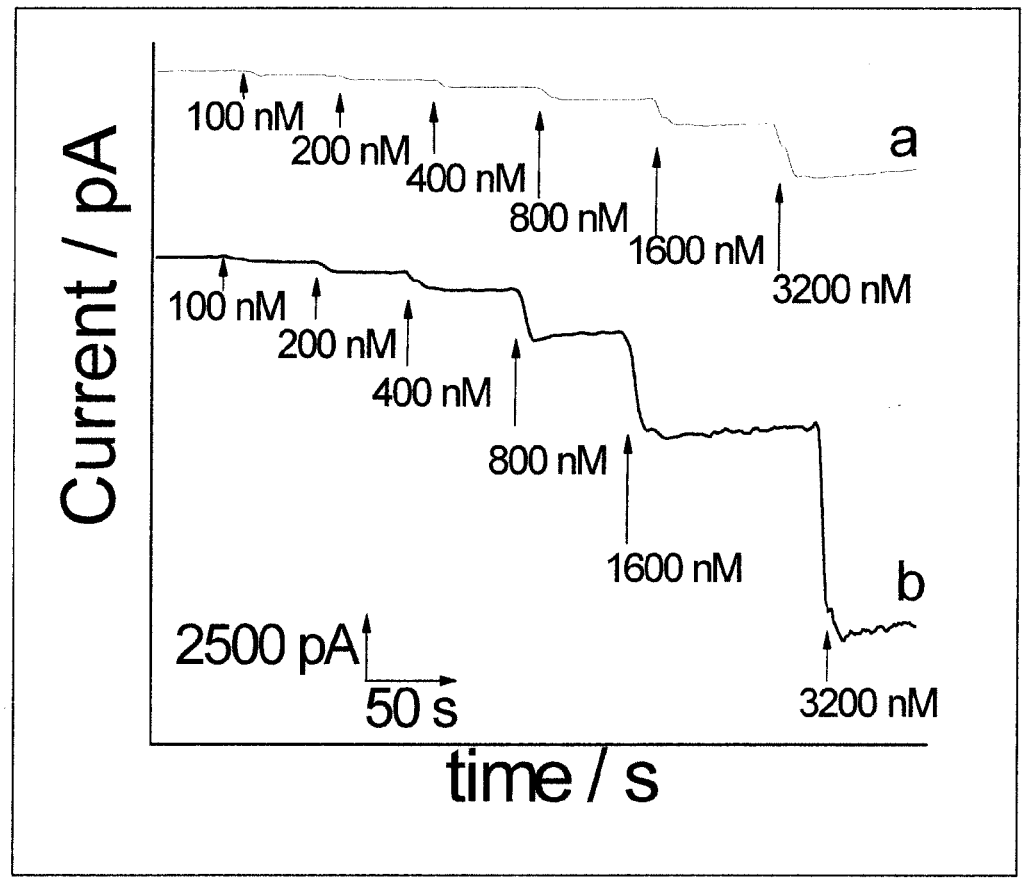
FIG. 18. Amperometric responses of bare (a) and RuO2-modified (b) Pt 10-μm fiber electrodes to additions of high nM aliquots of NO at + 0.8V vs. Ag/AgCl.

FIG.19. SEM images of bare (19A) and PEDOT-modified (19B) 30μm carbon fiber: 19C-D are figures for the 7μm fiber, with magnifications (19E).

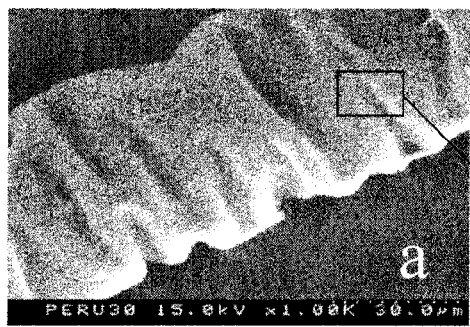 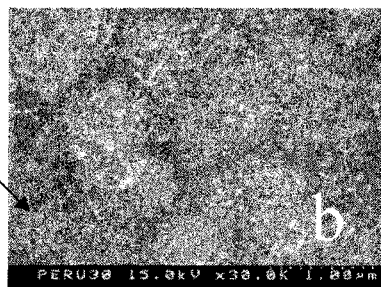
FIG. 20A  FIG. 20B
FIG. 20. SEM images for PEDOT-Ru modified 30-μm fiber at1000X (a) and 3000X (b) magnifications.

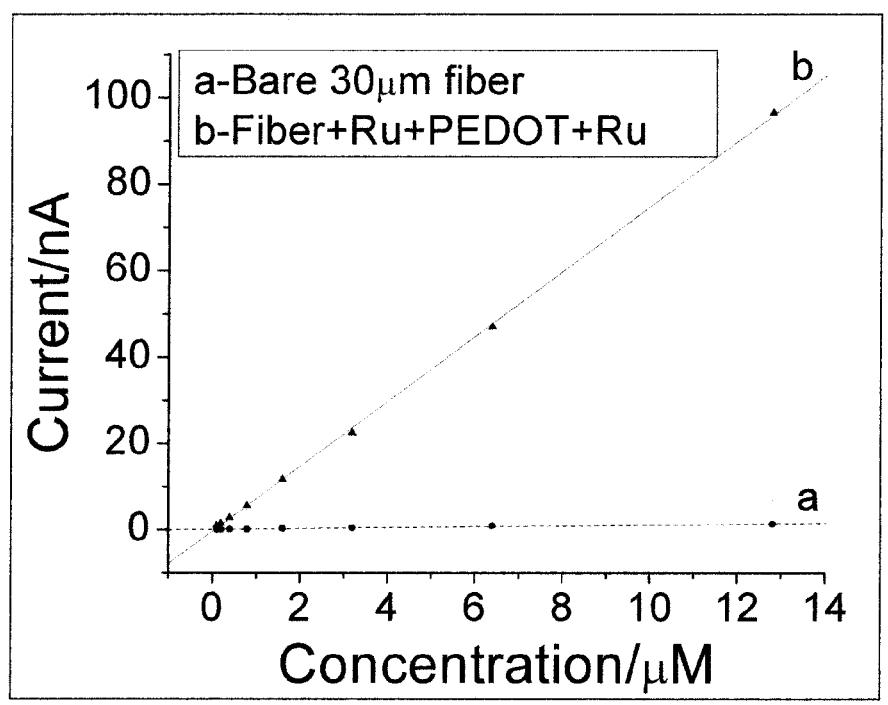
FIG.21A. Calibration plot from amperometric response of Ru-PEDOT-Ru-modified 30-μm carbon fiber.

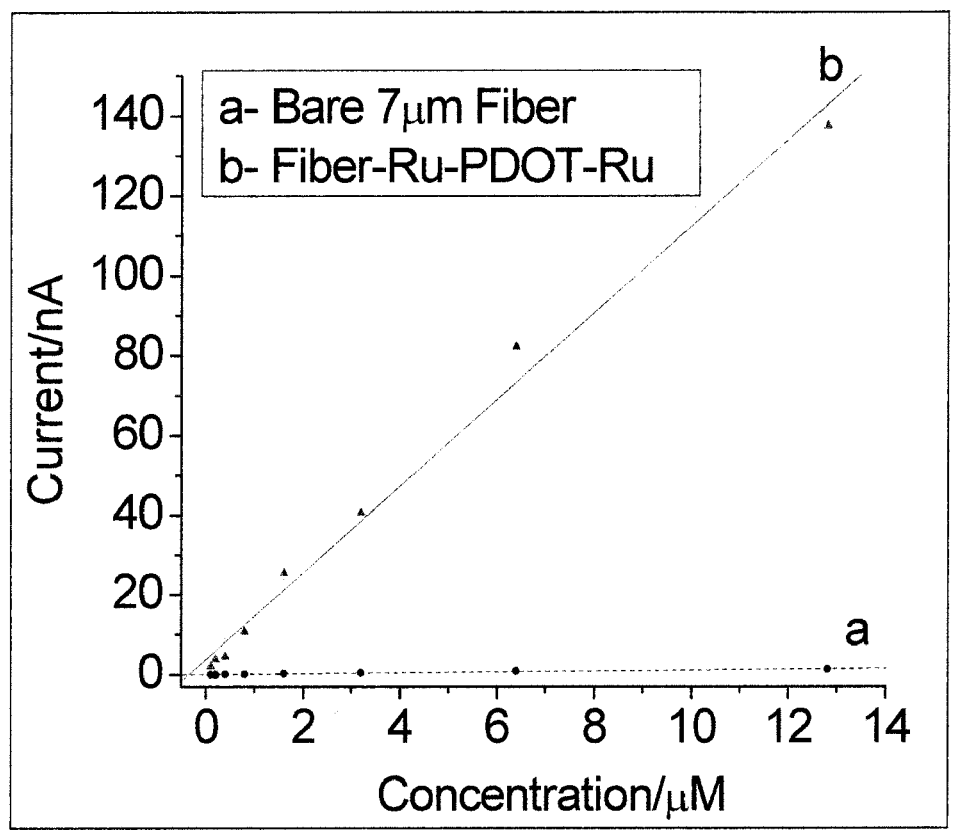
FIG. 21B. Calibration plot from amperometric response of Ru-PEDOT-Ru-modified 7-μm carbon fiber.

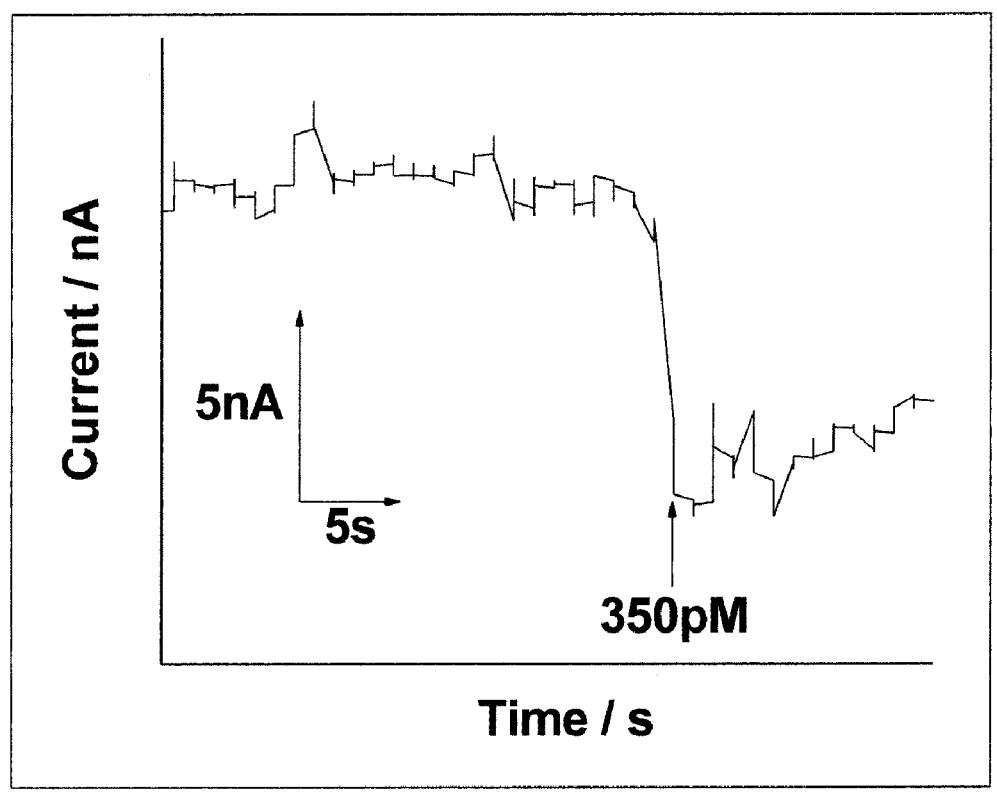
FIG. 22. Concentrations as low as 350 pM of NO can be detected on Ru-PEDOT-Ru modified CFE at +0.5V vs. Ag/AgCl.

NITRIC OXIDE SENSOR

CROSS REFERENCE TO RELATED APPLICATION

This application claims priority to and the benefit of U.S. Provisional Patent Application Ser. No. 60/853,603 filed Oct. 23, 2006 which application is incorporated herein by reference in its entirety.

BACKGROUND

The chemical compound nitric oxide is a gas with chemical formula NO. It is an important signaling molecule in the body of mammals, including humans, and is one of the few gaseous signaling molecules known.

Nitric oxide is a key biological messenger, playing a role in a variety of biological processes in the human body. It is also known as endothelium-derived relaxing factor ("EDRF") and is synthesized in vivo by a family of enzymes called nitric oxide synthases. It plays an important role in vasodilation, neurotransmission, and as part of the human immune response. For example, the endothelium of blood vessels uses nitric oxide to signal the surrounding smooth muscle to relax, thus dilating the artery and increasing blood flow. Nitric oxide is also used by plants.

Nitric oxide is also a toxic air pollutant produced by automobile engines and power plants.

The nitric oxide molecule is a free radical, which makes it very reactive and unstable. In air, it quickly reacts with oxygen to form nitrogen dioxide, signaled by the appearance of the reddish-brown color: $2\ NO + O_2 \rightarrow 2\ NO_2$.

One method of determining the concentration of nitric oxide is through electrochemistry. NO is oxidized by an electrode to induce a current change, which is proportional to concentration. However, there are some difficulties with this method. For example, a bare electrode is not selective and indiscriminately oxidizes multiple compounds. This results in interference and a poor NO signal, particularly in complex matrices (real media), such as biological media.

Some methods are known to increase the selectivity of an electrode. For example, selective membranes can be used with electrodes which exclude certain compounds from contact with the electrode. However, improvements are desirable.

BRIEF DESCRIPTION

Disclosed herein, in various embodiments, are various compositions and electrodes which are especially useful for measuring nitric oxide. Methods of making and using them are also disclosed.

In embodiments, a composition for measuring nitric oxide levels comprises ruthenium oxide nanoparticles, an electrically conductive powder, and a hydrophobic oil.

The electrically conductive powder may include a material selected from the group consisting of carbon, platinum, gold, and combinations thereof.

The weight ratio of ruthenium oxide nanoparticles to electrically conductive powder may be from about 1:5 to about 1:7. The hydrophobic oil may be a perfluorinated oil. The composition may further comprise poly(ethylenedioxythiophene).

In other embodiments, an electrode capable of detecting low levels of nitric oxide comprises ruthenium oxide nanoparticles.

The ruthenium oxide nanoparticles may be dispersed throughout the electrode.

The electrode may comprise a core and a surface coating, the ruthenium oxide nanoparticles being located in the surface coating. The core may be made from a material selected from the group consisting of carbon, platinum, gold, and combinations thereof.

The surface coating may have a thickness of from about 1 nanometer to about 1 micrometer.

The electrode may further comprise a second coating, the second coating comprising poly(ethylenedioxythiophene). The electrode may further comprise a third coating, the third coating also comprising ruthenium oxide nanoparticles, the second coating being located between the surface coating and the third coating.

The electrode may further comprise a membrane that is selective for nitric oxide, the membrane surrounding the electrode.

In other embodiments, a method for modifying an electrode to detect low levels of nitric oxide is disclosed, the method comprising:

providing an electrode and an acid solution, the acid solution comprising a ruthenium salt;

immersing the electrode in the acid solution; and cycling the potential of the acid solution between a first potential and a second potential for a period of time to form a coating comprising ruthenium oxide nanoparticles on the electrode.

The acid solution may have a pH of from about 2.0 to about 3.0. The concentration of the ruthenium salt in the acid solution may be from about 10 μM to about 50 μM.

The first potential may be about −0.85 V and the second potential may be about +0.65 V, vs. Ag/AgCl. The potential may be cycled at a rate of from about 80 V/sec to about 120 V/sec. The period of time may be from about 15 minutes to about 30 minutes.

In other embodiments, an electrode capable of detecting low levels of nitric oxide is disclosed, the electrode having a first coating thereon, the first coating comprising poly(ethylenedioxythiophene).

The electrode may further comprise a second coating, the second coating comprising ruthenium oxide nanoparticles. The first coating may have a thickness of about 300 nanometers or less.

In other embodiments, a method for detecting low concentrations of nitric oxide in a sample is disclosed, the method comprising:

providing an electrode comprising ruthenium oxide nanoparticles; and using the electrode to detect low concentrations of nitric oxide in a sample.

The electrode may be capable of detecting picomolar concentrations of nitric oxide.

These and other non-limiting characteristics of the disclosure are more particularly disclosed below.

BRIEF DESCRIPTION OF THE DRAWINGS

The following is a brief description of the drawings, which are presented for the purposes of illustrating the exemplary embodiments disclosed herein and not for the purposes of limiting the same.

FIG. 1 shows four voltammograms for various electrodes.

FIGS. 3A and 3B are graphs showing the response of a stationary electrode to various amounts of NO.

FIGS. 4A and 4B are graphs showing the response of a rotating disk electrode to various amounts of NO.

FIGS. 5A and 5B are graphs showing the response of an electrode to various amounts of NO.

FIG. 6 is a graph showing the detection limit of an electrode of the present disclosure.

FIGS. 7A and 7B are graphs showing the response of a rotating disk electrode to various amounts of NO at a lower applied potential.

FIG. 8 is a graph of cyclic voltammograms obtained during cyclic electrodeposition.

FIGS. 11A and 11B are a set of atomic force microscopy photos showing a surface before and after nanoparticle deposition.

FIG. 13 shows AES spectra of the surface of various electrodes.

FIGS. 14A-14D are graphs showing the response of microelectrodes to various amounts of NO.

FIGS. 15A and 15B are graphs showing the detection limit of a microelectrode of the present disclosure and a typical detection limit.

FIGS. 16A and 16B are graphs showing the results of FIA on various electrodes.

FIG. 18 is a graph showing the response of a platinum electrode to various amounts of NO.

FIGS. 20A and 20B are SEM images of an electrode having a PEDOT coating and a ruthenium oxide coating.

FIGS. 21A and 21B show the sensitivity of electrodes having multiple coatings of ruthenium oxide and PEDOT.

FIG. 22 is a graph showing the detection limit of a three-layer electrode of the present disclosure.

DETAILED DESCRIPTION

Figure 2A:
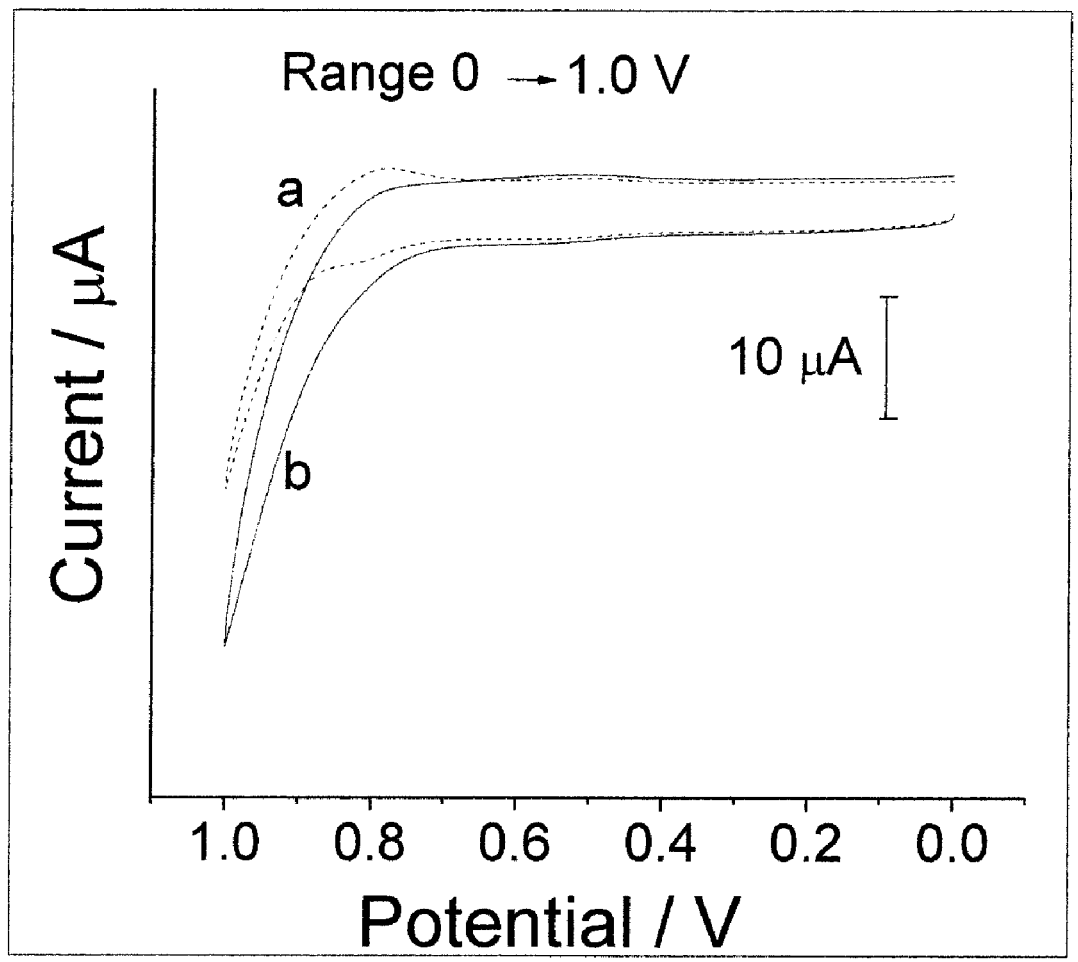
FIGS. 2A and 2B show two voltammograms obtained over different potential ranges.

A more complete understanding of the compositions, processes, and devices disclosed herein can be obtained by reference to the accompanying drawings. These figures are merely schematic representations based on convenience and the ease of demonstrating the present disclosure, and are, therefore, not intended to indicate relative size and dimensions of the devices or components thereof and/or to define or limit the scope of the exemplary embodiments.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The term "nano" as used in "nanoparticles" indicates a particle size of less than 1000 nanometers. The particle size is measured as the average diameter of nanoparticles having the same composition. In embodiments, nanoparticles have a particle size of from about 30 nm to about 500 nm. In further embodiments, the nanoparticles have a particle about 80 nm to about 150 nm.

The compositions, devices, and processes of the present disclosure are especially useful when applied to electrodes for the monitoring of nitric oxide in both in vivo and in vitro environments. Monitoring nitric oxide levels is critical to a number of biomedical and environmental applications. Such electrodes are more sensitive and reliable than existing electrodes, allowing for detection of nitric oxide at the picomolar level, prior to any additional optimization using selective membranes.

The present disclosure encompasses the use of ruthenium oxide in electrodes. The electrodes are particularly suited for measuring nitric oxide concentrations. Generally, ruthenium oxide may be present as $RuO_2$ or $RuO_4$.

In one embodiment, a composition comprises ruthenium oxide nanoparticles, an electrically conductive powder, and a hydrophobic oil. This composition can be used to make a paste electrode containing ruthenium oxide. The electrically conductive powder includes a material selected from the group consisting of carbon, platinum, gold, and combinations thereof. The hydrophobic oil is used to bind the nanoparticles and electrically conductive powder together. The hydrophobic oil also helps nitric oxide partition into the paste electrode, increasing the local NO concentration and thus the electrode's sensitivity. Suitable hydrophobic oils include perfluorinated oils. Another exemplary hydrophobic oil is Kel-F oil, available from multiple commercial sources.

In embodiments, the weight ratio of ruthenium oxide nanoparticles to electrically conductive powder in the composition is from about 1:5 to about 1:7. The weight ratio of ruthenium oxide nanoparticles to hydrophobic oil in the composition is from about 1:2 to about 1:4. An optimal ratio for the composition is 6:3:1 w/w/w conductive powder:hydrophobic oil:ruthenium oxide nanoparticles.

In some embodiments, the composition may further comprise a sulfur-containing polymer. Exemplary sulfur-containing polymers include polythiophenes and polymers containing thiol pendant groups. In particular embodiments, the composition further comprises a polythiophene polymer. A particularly suitable polythiophene polymer is poly(3,4-ethylenedioxythiophene), commonly abbreviated as PEDOT.

An electrode comprising ruthenium oxide nanoparticles can be made from the composition described. The nanoparticles are generally evenly dispersed throughout the electrode. Such macroelectrodes generally have a size of 1 mm or above.

In alternative embodiments, an electrode has a coating thereon, the coating comprising ruthenium oxide nanoparticles. Again, the electrode itself is generally made from a conductive material, such as carbon, platinum, and gold. These electrodes can be coated in a plating solution containing ruthenium salts as the ruthenium oxide precursor. Exemplary ruthenium salts include, but are not limited to, $RuF_3$, $RuF_4$, $RuF_6$, $(RuF_5)_4$, $RuCl_2$, $RuCl_3$, $RuBr_2$, $RuBr_3$, $RuI_2$, and $RuI_3$. The coating solution is used to electrochemically deposit ruthenium onto the electrode using either volammetric cycling or controlled potential chronoamperometry. There, the ruthenium oxidizes into ruthenium oxide nanoparticles. The coating of ruthenium oxide can have a thickness from as low as about 1 nanometer up to about 2 µm. In more specific embodiments, the thickness of the coating is 1 µm or less. This method is useful for macroelectrodes and is particularly suitable for microelectrodes (having a diameter below 1 mm). Such coatings have been successfully deposited on carbon fibers and platinum fibers as small as 7 microns in size.

More specifically, the coating is made by forming an acid solution containing at least one ruthenium salt. In embodiments, the acid solution has a pH from about 2.0 to about 3.0. $HClO_4$ is an exemplary acid. The concentration of the ruthenium salt(s) in the acid solution is from about 10 µM to about 50 µM. In more specific embodiments, the concentration of the ruthenium salt(s) is from about 20 µM to about 50 µM. The salt concentration can be adjusted depending on the size of the electrode so as to avoid saturation of the electrode surface and consequent loss of the nanostructure of the ruthenium nanoparticle clusters formed. The potential of the acid solution is then cycled between a first potential and a second potential for a given period of time to form ruthenium oxide nanoparticles on the electrode surface. In embodiments, the potential is cycled between about −0.85 V and about +0.65 V vs. Ag/AgCl. In other embodiments, the difference between the first and second potentials is from about 1 V to about 2 V. In other embodiments, the difference between the first and second potentials is about 1.5 V. In still other embodiments, the difference between the first and second potentials is at least 1.5 V. In other embodiments, the first potential is negative vs. Ag/AgCl and the second potential is positive vs. Ag/AgCl. The potential can be cycled at a rate of from about 80 V/sec to about 120 V/sec and in specific embodiments is cycled at a rate of about 100 V/sec. The rate of cycling can also help in avoiding quick growth of large ruthenium oxide aggregates and saturating the surface of the electrode. The potential can be cycled for a period of from about 15 minutes to about 30 minutes, or for about 20 minutes. This coating process occurs at room temperature.

In further embodiments, the electrode may further comprise a second coating, the second coating comprising poly (3,4-ethylenedioxythiophene) (PEDOT). The second coating may be below or above the coating comprising ruthenium oxide nanoparticles. The PEDOT coating itself has a cauliflower-like structure, compared to the granular structure of the ruthenium oxide coating. The PEDOT coating can be laid on the electrode via cyclic voltammetry as well.

In further embodiments, there can be multiple alternating layers of ruthenium oxide coatings and PEDOT coatings. In specific embodiments, the electrode is coated with ruthenium oxide, then PEDOT, then another coating of ruthenium oxide.

In other alternative embodiments, an electrode has a coating thereon, the coating comprising poly(3,4-ethylenedioxythiophene) (PEDOT). The PEDOT coating may be applied to the electrode via cyclic voltammetry. However, the potential range for the cycling is from about +1.5 V to about −1.5 V vs. Ag/AgCl and the cycling can range at a rate of from about 200 to about 300 mV/sec, or about 250 mV/sec. The coating solution in which the electrode is immersed comprises an organic solvent and optionally an electrolyte that supports charge transport if the organic solvent has low conductivity. An exemplary coating solution contains 0.5M 3,4-ethylenedioxythiophene in the presence of 0.1M tetrabutyl ammonium tetrafluoroborate in acetonitrile. The thickness of the PEDOT coating may be about 300 nm or less, or about 200 nm.

In further embodiments, a selective membrane can be used in conjunction with the electrode containing a ruthenium oxide coating. Selective membranes are generally measured in terms of selectivity for a given compound and permeability for the given compound. The membrane should be selective for nitric oxide. Suitable membranes include NAFION (available from DuPont) and those available from WPI.

Electrodes containing ruthenium oxide are especially suitable for detecting nitric oxide. They are highly selective for nitric oxide and have high sensitivity. They exhibit a practical detection limit as low as 100 pM, with a linear range extending to about the 100 µM range. In contrast, current electrodes have practical detection limits in the 40-80 nM range. The electrodes of this disclosure may also be suitable for detecting nitric oxide in gas phase as well as in solution.

Nitric oxide is sensed and quantified via an electrocatalytic oxidation process mediated by the ruthenium oxide nanoparticles. Ruthenium oxide nanoparticles have anodic and cathodic peaks around ~0.5 V compared to Ag/AgCl; these peaks are very close to the redox couple assigned to $Ru^{3+}/Ru^{4+}$. Another redox couple that is easily identified at higher positive potentials, ~0.8 V, is assigned to $Ru^{4+}/Ru^{6+}$. The addition of NO causes the anodic current of the $Ru^{4+/6+}$ couple to increase with concomitant loss of reversibility. This behavior is a typical signature of an electrocatalytic process triggered by the oxidation of NO on ruthenium oxide-containing electrodes. The amperometric response to oxidation of NO on a ruthenium oxide-containing electrode is significantly higher compared to a bare electrode, even at potentials less positive than +0.5 V.

The following examples are for purposes of further illustrating the present disclosure. The examples are merely illustrative and are not intended to limit devices made in accordance with the disclosure to the materials, conditions, or process parameters set forth therein. All parts are percentages by volume unless otherwise indicated.

EXAMPLES

Preparations for Examples 1-7

Carbon paste was prepared by thoroughly hand mixing graphite powder and Kel-F oil (6:4 w/w). This carbon paste was used as the control.

Ruthenium oxide modified carbon paste (optimized ratio 6:3:1 w/w graphite/oil/ruthenium oxide) was prepared by adding weighed amounts of ruthenium oxide and graphite powder to 10 ml of diethylether. The mixture was sonicated until all the diethylether was evaporated. Then the desired amount of Kel-F oil was added.

Electrodes were made by packing the appropriate resulting paste tightly into the cavity of hollow electrodes (BAS 3 mm diameter/2 mm depth or 1 mm diameter/1 mm depth; Model MF-2010 and MF-2015h respectively). Finally, the electrode surface was smoothed. Rotating disc electrodes were constructed using RDE empty tips (4 mm diameter, Brinkmann Inc.) filled with the appropriate paste in a similar fashion.

Example 1

Electrodes were placed in a pH 7.0 phosphate buffer solution. Voltammograms were obtained in (1) the phosphate buffer solution; and (2) with 4 µM nitric oxide added to the phosphate buffer solution.

FIG. 1 shows the four voltammograms obtained. Line a is the control electrode in the absence of 4 µM NO. Line b is the control electrode in the presence of 4 µM NO. Line c is the ruthenium oxide modified electrode in the absence of 4 µM NO. Line d is the ruthenium oxide modified electrode in the presence of 4 µM NO. The oxidation potential of NO on the control electrode at about +1.15 V vs. Ag/AgCl correlates with NO oxidation measured on solid graphite electrodes. In the presence of ruthenium oxide, the oxidation of NO occurs at a less positive potential and with larger currents.

Example 2

Figure 2B:
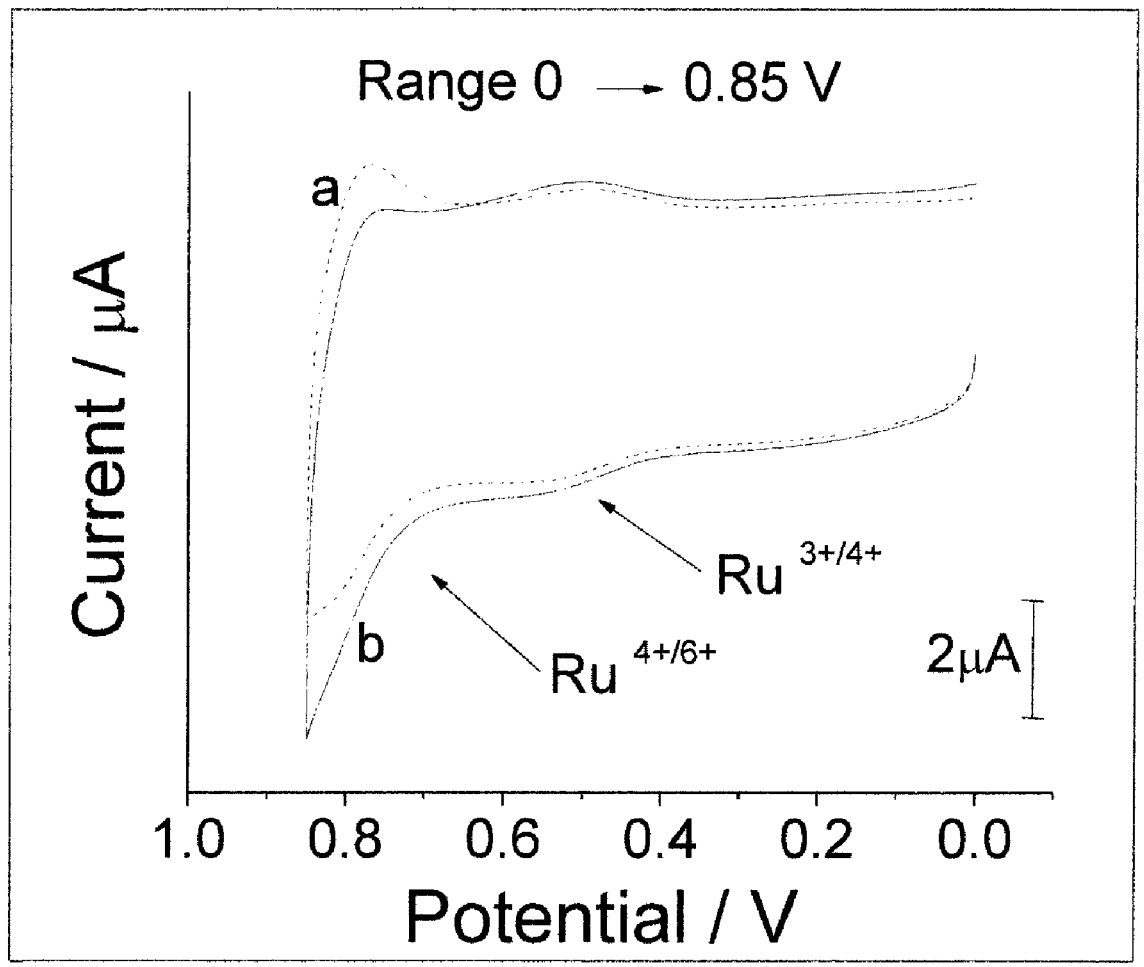

The broad nature of the voltammetric responses of the modified electrode suggests that changes in oxidation states for the ruthenium oxide particles occur over wide potential ranges. Cyclic voltammograms were obtained with an ruthenium oxide modified electrode over two different potential ranges. FIG. 2 shows the obtained voltammograms. In FIG. 2A, the potential range was from 0 to 1.0 V. In FIG. 2B, the potential range was from 0 to 0.85 V. In both FIGS. 2A and 2B, line a is the electrode in the absence of 4 μM NO and line b is the electrode in the presence of 4 μM NO, both in pH 7.0 phosphate buffer solution. The subtle anodic and cathodic peaks around 0.5 V vs. Ag/AgCl are very close to the redox couple assigned previously to $Ru^{3+}/Ru^{4+}$. Another redox couple was easily identified at about +0.8 V, and was assigned to the $Ru^{4+}/Ru^{6+}$ couple.

Example 3

Constant potential amperometry was used to investigate the response of modified electrodes to varying amounts of NO. Control and ruthenium oxide modified electrodes were exposed to aliquots of 2 μM, 4 μM, 6 μM, 8 μM, and 10 μM NO with stirring (250 rpm) in pH 7.0 phosphate buffer solution and the response was measured at an applied potential of 0.8 V vs. Ag/AgCl. FIG. 3 shows the results. In FIG. 3A, the amperometric response is shown. Line a is the control electrode and line b is the modified electrode. The modified electrode exhibited a significantly enhanced electrochemical response compared to the control electrode. FIG. 3B is a graph of the amperometric response vs. NO concentration. The sensitivity for the modified electrode was approximately 10 times that of the control electrode, and ranged from 85 to 100 pA/nM at +0.8 V potential.

Example 4

Rotating disk electrodes were tested instead of stationary electrodes in a manner similar to that of Example 3. The rotation rate was 2000 rpm and the applied potential was 0.8 V vs. Ag/AgCl. The electrodes were exposed to aliquots of 256 nM, 512 nM, 1024 nM, 2048 nM, and 4096 nM NO added to pH 7.0 phosphate buffer solution. In FIG. 4A, the amperometric response is shown. Line a is the control electrode and line b is the modified electrode. Again, the modified electrode exhibited a significantly enhanced electrochemical response compared to the control electrode. FIG. 4B is a graph of the amperometric response vs. NO concentration. The sensitivity for the modified electrode was in the range of 750 to 1000 pA/nM at +0.8 V potential.

Example 5

Another experiment was carried out as in Example 4, except that the aliquots were 1 nM, 2 nM, 4 nM, 8 nM, and 16 nM NO. The sensitivity for the modified electrode was about 6100 pA/nM at +0.8 V potential. The results are shown in FIG. 5. Line a is the control electrode and line b is the modified electrode.

Example 6

The detection limit of the ruthenium oxide modified electrode was determined. Using a composition of 6:3:1 graphite/Kel-F/ruthenium oxide at +0.8 V, a detection limit of 100 pM NO was measured in pH 7.0 phosphate buffer solution, based on a minimum S/N ratio of 3, as shown in FIG. 6.

Example 7

In addition to sensitivity, selectivity is also important for electrochemically determining NO concentrations. Generally, at high applied potentials, other electroactive biological species may also be oxidized. Thus, using low potentials may also increase sensitivity by avoiding interference through a potential-based selectivity. Normally, the applied potential used to detect NO is between +0.85 and +1.1 V vs. Ag/AgCl. Nitrite anion, which usually oxidizes at ~+0.9 V vs. Ag/AgCl, is the most common interfering species for NO determination on carbon and/or platinum based electrodes.

Another experiment was carried out as in Example 4, except that the aliquots were 2 μM, 4 μM, 6 μM, 8 μM, and 10 μM NO and the response was measured at an applied potential of 0.5 V vs. Ag/AgCl. FIG. 7 shows the results. Line a is the control electrode and line b is the modified electrode. At this lower potential, the modified electrode maintained the increase in sensitivity with good linear response. At this relatively low potential, nitrite interference was also significantly diminished.

Preparations for Examples 8-16

Carbon fiber microelectrodes (7 μm or 30 μm in diameter) were prepared using published procedures. Briefly, single fibers were isolated and sonicated in acetone, 50% nitric acid, and distilled water. A dried fiber was then mounted at the end of a copper wire and fixed with conductive epoxy. The mounted carbon fiber was inserted into a pulled glass capillary and sealed with non-conductive epoxy leaving about 3 mm fiber protruding. The copper wire was then fixed to the stem of the glass tube with the epoxy glue. The pulled end of the glass capillary was coated with Ag/AgCl ink. A layer of insulating material was placed over the body of the sensor leaving 2 mm of the Ag/AgCl reference electrode exposed. The freshly prepared carbon fiber electrode was then immersed in a 10 mM $HClO_4$ acid containing 20 μM $RuCl_3$, and the potential was cycled between −0.85 V and +0.65 V vs. Ag/AgCl at 100 V/s over 20 minutes. This generated ruthenium oxide nanoparticles on the surface of the exposed carbon fiber tip. The electrode was then gently washed with nanopure-deionised water and allowed to dry before use.

Example 8

Cyclic voltammograms were obtained during the immersion of a 7 μm carbon fiber electrode in a 20 μM $RuCl_3$/10 mM $HClO_4$ acid solution. FIG. 8 shows these cyclic voltammograms during cyclic electrodeposition. For clarity, only the initial portion of the modification is shown and each line (a-f) represents 100 cycles (between −0.85 V and +0.65 V). The curves were recorded every 3 seconds.

Lines a and b show that during the early stages of the modification, the reduction current increases only in the region of the most negative potentials used (−0.65 to −0.85 V). This appeared to trigger the initial nucleation of ruthenium material on the carbon fiber surface. The reduction current then started to increase rapidly at less negative potentials, as seen in lines c through f. The backward oxidation current also increased at less positive potentials. Presumably, after the formation of slowly growing ruthenium nuclei on the carbon surface, additional electrode processes led to the electrodeposition of ruthenium oxides. The voltammetric current increased to a maximum value in the 20-min period of continuous cycling (not shown).

Example 9

Field emission scanning electron microscopic (FESEM) images of bare and modified electrodes are shown in FIG. 9.

Figure 9A:
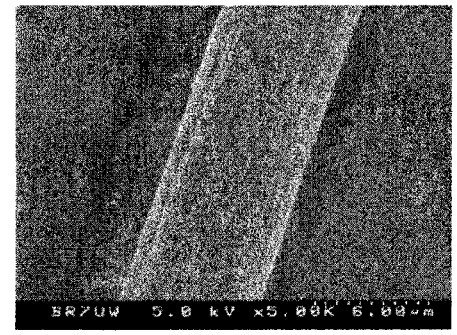
FIGS. 9A-9F show SEM images of various aspects of some electrodes.
Figure 9B:
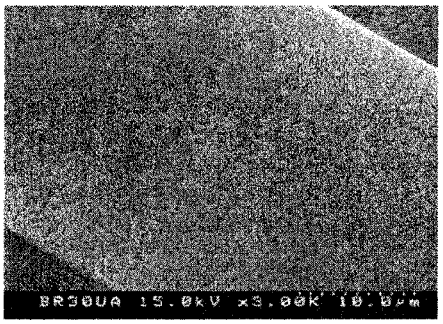
Figure 9C:
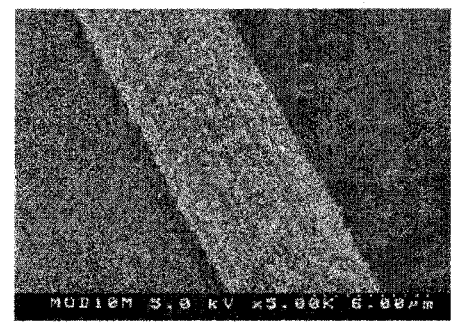
Figure 9D:
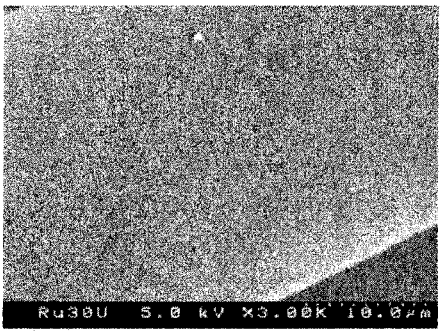
Figure 9E:
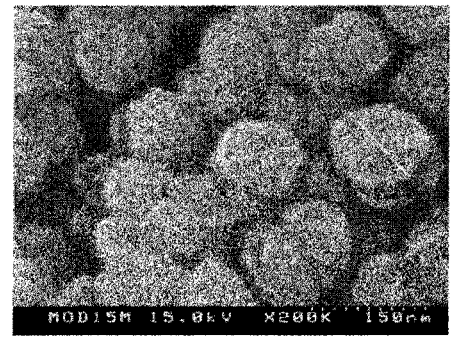
Figure 9F:
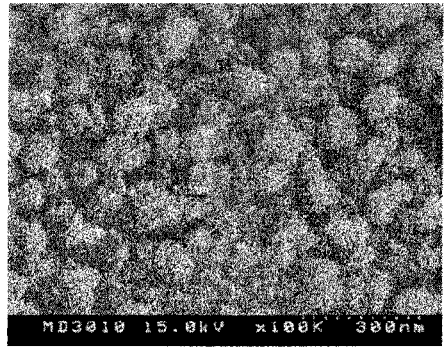

FIG. 9A shows the smooth surface of a bare 7-μm carbon fiber. FIG. 9B shows the smooth surface of a bare 30-um carbon fiber. FIG. 9C shows the surface of a ruthenium oxide modified 7-μm electrode. FIG. 9D shows the surface of a ruthenium oxide modified 30-μm electrode. The difference in smoothness is evident. FIGS. 9E and 9F are high-magnification images of the surface of a 7-μm and 30-μm electrode respectively; ruthenium oxide nanoparticles are evident in these photos. Some of the particles in FIGS. 9E and 9F were measured as having diameters of 79.2 nm, 102.7 nm, 114.6 nm, 99 nm, and 103 nm.

Example 10

Figure 10:
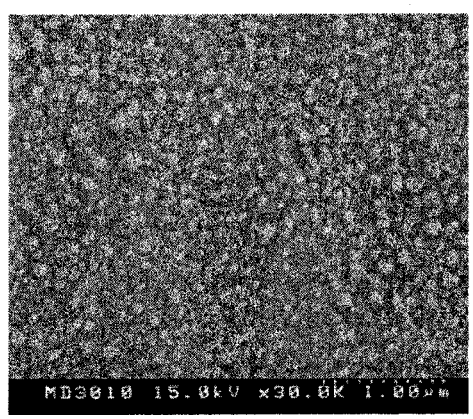
FIGS. 10A-10C show the particle distribution of ruthenium oxide on an electrode at various times.
Figure 10:
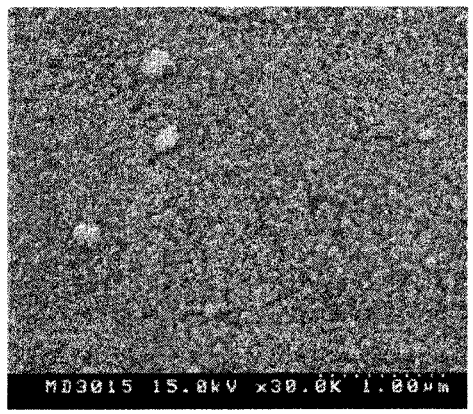
Figure 10:
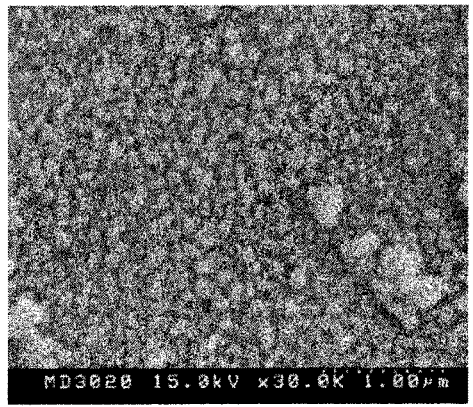

FIG. 10 is three FESEM images showing the particle distribution of ruthenium oxide over time at 10 min (FIG. 10A), 15 min (FIG. 10B), and 20 min (FIG. 10C), respectively. The particle density clearly increased with deposition time, and full coverage of the carbon fiber electrode appeared to be achieved after 20 minutes of deposition time.

Example 11

Atomic force microscopy (AFM) was also used to characterize the early stages of ruthenium oxide nanoparticle growth as they formed using the electrodeposition technique. FIG. 11A shows the surface of a highly oriented pyrolitic graphite (HOPG) used as the substrate prior to deposition, and FIG. 11B shows the surface of the substrate after deposition. The deposit possessed a rough morphology containing many small spherical grains aggregated to form larger oxide particles with a height of about 2 nanometers.

Example 12

Figure 12:
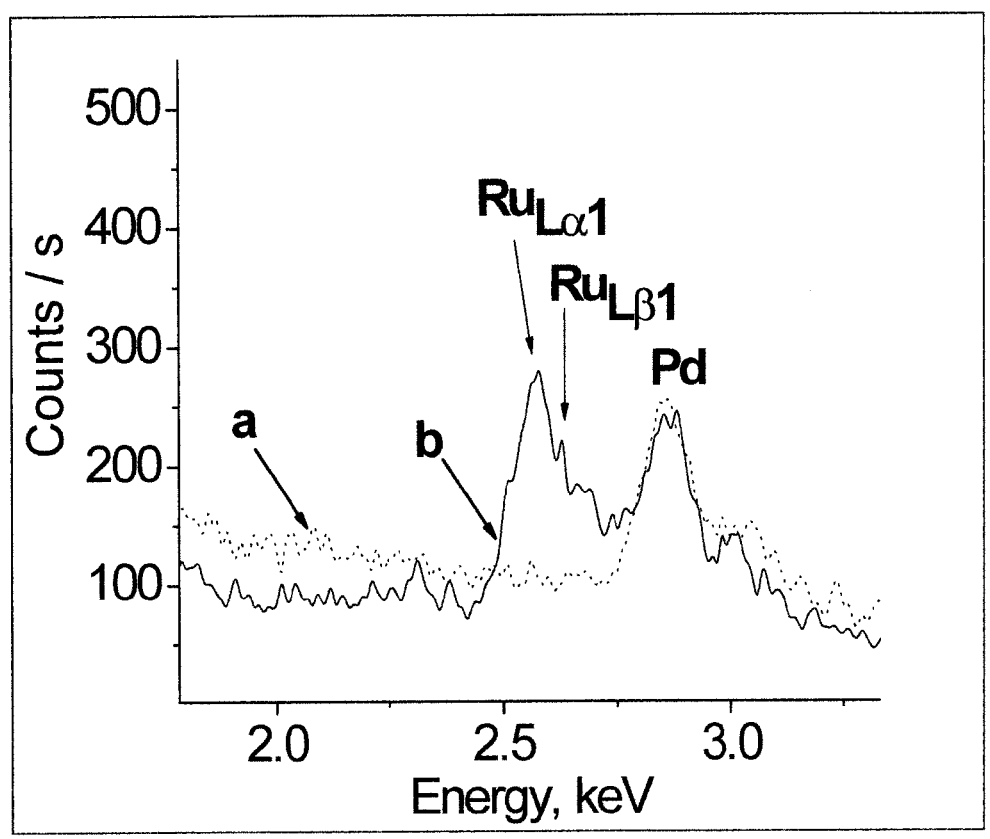
FIG. 12 shows the spectra of the surface of various electrodes.

The surface composition of the ruthenium oxide modified electrode was also characterized by energy dispersive x-ray spectroscopy (EDX). FIG. 12 shows the spectra of a bare electrode (line a) and a ruthenium oxide modified electrode (line b) after 15 minutes palladium sputter coating. The two most intense transitions for Ru, $L\alpha^1$ and $L\beta^1$, correlate with reported values. No peaks are observed in that region for the bare electrode. The ruthenium elemental composition is less than expected, but not surprising because EDX probes go deeper in the material and x-rays are produced in a pear-shaped volume up to 4-5 μm in diameter. The observed thickness of the ruthenium oxide layer is less than 1 μm.

Example 13

Auger electron spectroscopy was used to quantify the surface modification. FIG. 13 shows AES spectra of a bare electrode (dotted line) and a ruthenium oxide modified electrode (solid line), both 7 μm in diameter. The Auger electron peaks of ruthenium at 273 eV ($Ru_1$) and carbon at 272 eV ($C_1$) closely resemble each other. The ruthenium oxide modified electrode also displays Auger electron peaks at 231 ($Ru_2$), 200, 184, 176 and 150 eV. The $Ru_2$ peak can be used for accurate surface composition determination which shows that the surface of the modified electrode contains 95.5% of ruthenium and 4.5% of oxygen.

Example 14

Electrocatalytic oxidation of NO on ruthenium oxide modified carbon fiber electrodes was assessed using constant potential time-based amperometry. FIGS. 14 and 15 illustrate typical staircase curves obtained with modified electrodes at 0.80 V vs. Ag/AgCl using the same procedure as Example 4. For FIGS. 14A and 14B, aliquots of 1 μM, 2 μM, 4 μM, 6 μM, 8 μM, and 10 μM NO were used. For FIGS. 14C and 14D, the aliquots were 100 nM, 200 nM, 400 nM, 600 nM, 800 nM, and 1000 nM NO. For both, line a was the control electrode and line b was the modified electrode. A rapid response time is important for sensitive NO quantification. For the modified electrodes, 95% of the response was observed in less than 10 seconds as seen in FIGS. 14A and 14C. The linear range of the modified electrodes extended over three orders of magnitude, from nM to μM NO, as seen in FIGS. 14B and 14D. The sensitivities for the modified electrodes were 1.0 to 2.0 pA/nM, which was 10-15 times higher than the control electrodes (0.09-0.15 pA/nM). These results are attributed to more efficient electrocatalytic oxidation of NO by the deposited ruthenium oxide nanoparticles on the carbon fiber surface.

Example 15

Figure 15B:
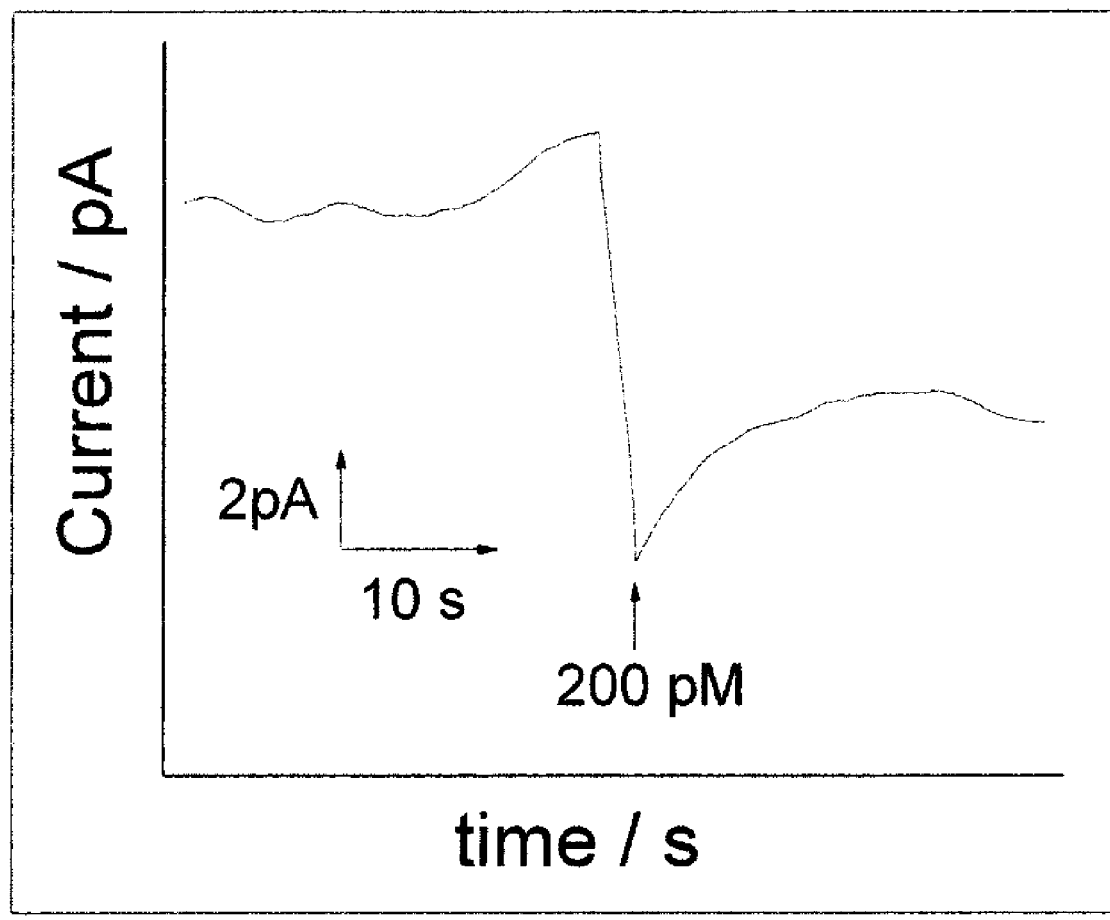

The detection limit of the ruthenium oxide modified electrode was determined. The sensitivity of an electrode depends largely on its reactive surface area and the electrode materials used in the design. An electrode with a small reactive surface area will generally have a lower sensitivity compared to one with a larger surface area. The ruthenium oxide nanoparticles provide a larger reactive surface area. A detection limit of 200 μM NO was measured in pH 7.0 phosphate buffer solution, based on a minimum S/N ratio of 3 at an applied voltage of +0.8 V, as shown in FIG. 15A. FIG. 15B shows the typical detection lmit at 200 pM NO in pH 7.0 phosphate buffer solution. Based on these results, a detection limit as low as 50 μM should be achievable.

Example 16

Flow Injection Analysis (FIA) is an automated, continuous flow approach to perform chemical analysis, based on injecting a small, well-defined volume of sample into a continuously flowing inert carrier stream of solvent. At physiological conditions, NO quickly diffuses and create concentration gradients. To mimic actual flux of NO in the biological systems, dynamic NO quantification was carried out using flow injection analysis.

FIG. 16 shows the result of FIA performed on bare electrodes and modified electrodes of 30 μm in diameter. Aliquots of 50 nM, 100 nM, 200 nM, 300 nM, 400 nM, 800 nM, 400 nM, 300 nM, 200 nM, 100 nM, and 50 nM were sequentially added to a pH 7.0 phosphate buffer solution. In FIG. 16A, the amperometric response is shown. Line a is the control electrode and line b is the modified electrode. FIG. 16B is a graph of the charge response vs. NO concentration. The sensitivity of the modified electrode was 1.1 μC/nM, which is about 10-15 times greater than the bare electrode.

Example 17

Figure 17A:
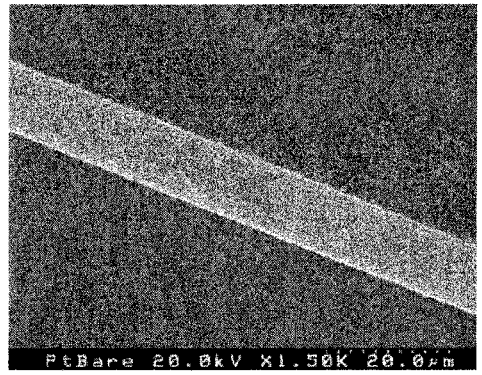
FIGS. 17A-17D are SEM images of electrodes prepared using platinum fibers.
Figure 17B:
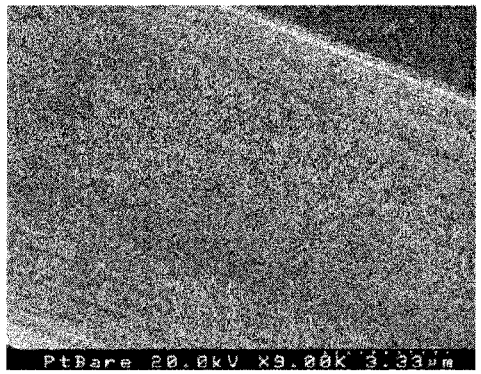
Figure 17C:
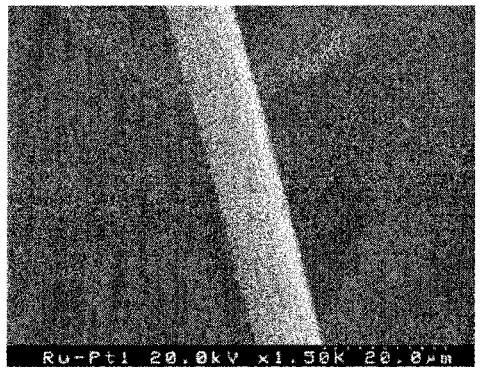
Figure 17D:
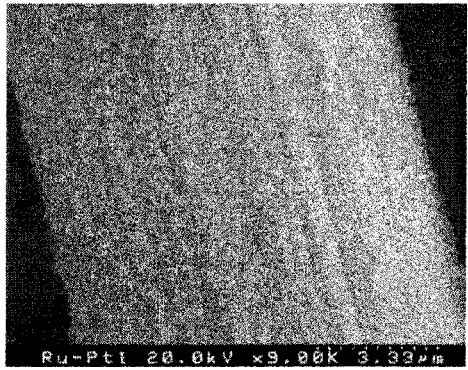

Microelectrodes were prepared using platinum fibers instead of carbon fibers. FIG. 17 shows SEM images of the platinum fiber electrodes. FIGS. 17A and 17B show the smooth surfaces of a bare 10-μm platinum fiber. FIG. 17C shows a ruthenium oxide modified platinum fiber and FIG. 17D is a high-magnification image wherein the ruthenium oxide particles are clearly visible.

FIG. 18 shows the amperometric response of a platinum electrode in response to aliquots of 100 nM, 200 nM, 400 nM, 800 nM, 1600 nM, and 3200 nM NO added to a pH 7.0 phosphate buffer solution at an applied potential of +0.8 V vs. Ag/AgCl.

Example 18

Figure 19A:
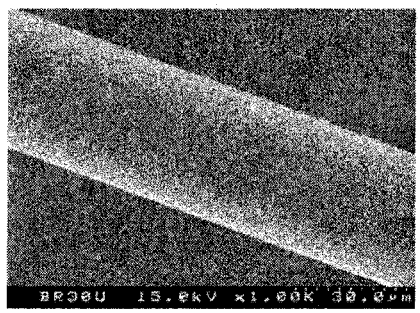
FIGS. 19A-19E show various aspects of electrodes having a PEDOT coating.
Figure 19B:
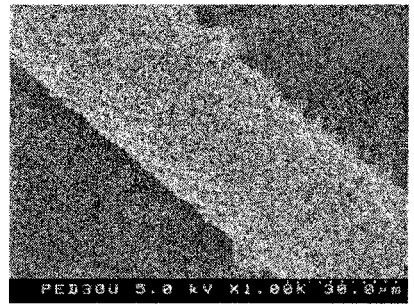
Figure 19C:
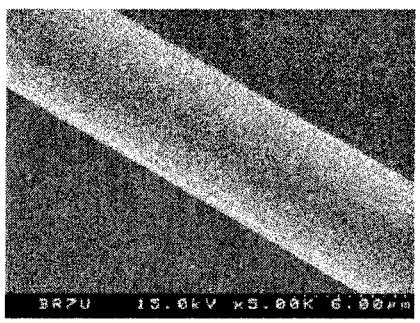
Figure 19D:
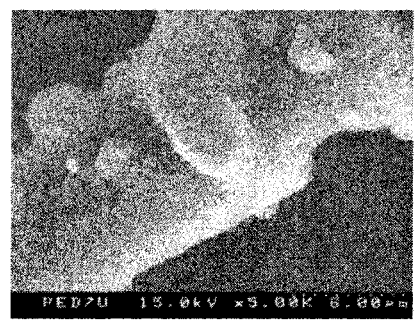
Figure 19E:
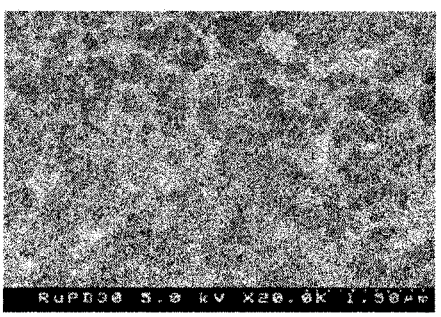

Electrodes were prepared which contained a PEDOT coating. FIG. 19 shows SEM photos of such electrodes. FIGS. 19A and 19C are bare electrodes of 30 μm and 7 μm in diameter, respectively. FIGS. 19B and 19D show the surface of PEDOT-modified electrodes, respectively. FIG. 19E shows the PEDOT surface at high magnification.

An electrode was also prepared which had a PEDOT coating laid down on the electrode surface, then a ruthenium oxide coating laid down on the PEDOT coating. FIG. 20A shows the surface of this electrode and FIG. 20B shows the surface at high magnification. The granular ruthenium oxide particles are visible on the PEDOT coating.

Example 19

Electrodes were prepared which had a ruthenium oxide coating laid on the fiber electrode surface, a PEDOT coating laid on the ruthenium oxide coating, and a second ruthenium oxide coating laid on the PEDOT coating (i.e., fiber-Ru-PEDOT-Ru). The amperometric response for these 3-layer electrode was compared to a bare electrode at applied potential of +0.5V vs. Ag/AgCl. FIG. 20A is a graph of response vs. concentration for a fiber 30 μm in diameter and FIG. 20B is a graph of response vs. concentration for a fiber 7 μm in diameter. The sensitivity of the three-layer electrode 30 μm in diameter was about 70 times greater than the bare electrode. The sensitivity of the three-layer electrode 7 μm in diameter was about 100 times greater than the bare electrode.

The detection limit of the three-layer electrode was determined. A detection limit of 350 pM NO was measured in pH 7.0 phosphate buffer solution, based on a minimum S/N ratio of 3, at an applied voltage of 0.5 V, as shown in FIG. 22 Limits as low as about 50 pM should be achievable with shielded potentiostats and higher applied voltages. This detection limit is already much lower than those reported in the literature for NO (40-80 nM).

Example 20

Figure 23:
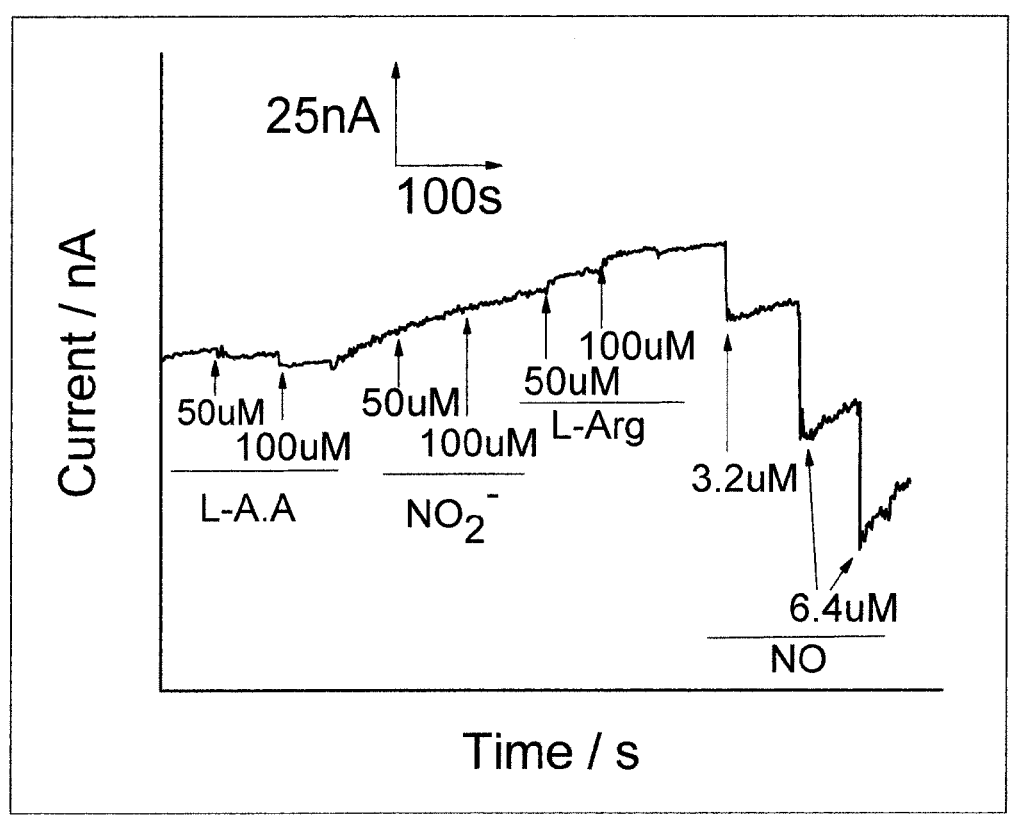
FIG. 23 is a graph showing the selectivity of an electrode containing a selective membrane coating.

A three-layer electrode (fiber-Ru-PEDOT-Ru) was further covered with a coating of NAFION, a copolymer of poly(tetrafluoroethylene) and perfluoro-3,6-dioxa-4-methyl-7-octene-sulfonic acid. The electrode was then exposed to aliquots of 50 μM and 100 μM ascorbic acid, nitrite, and L-arginine. After those exposures, the electrode was exposed to aliquots of 3.2 μM and 6.4 μM NO. The applied potential was +0.5 V vs. Ag/AgCl. The amperometric response is shown in FIG. 23. As can be seen, the electrode was highly selective against ascorbic acid, nitrite, and L-arginine. It also continued to be highly sensitive to NO.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

The invention claimed is:

1. An electrode capable of detecting low levels of nitric oxide, the electrode comprising:
   a core made from a material selected from the group consisting of carbon, platinum, gold, and combinations thereof;
   a surface coating consisting of ruthenium oxide nanoparticles upon the core; and
   a second coating upon the surface coating, the second coating comprising poly(ethylenedioxythiophene).

2. The electrode of claim 1, wherein the surface coating has a thickness of from about 1 nanometer to about 1 micrometer.

3. The electrode of claim 1, further comprising a third coating, the third coating also comprising ruthenium oxide nanoparticles, the second coating being located between the surface coating and the third coating.

4. The electrode of claim 1, further comprising a membrane that is selective for nitric oxide, the membrane surrounding the electrode.

5. A method for detecting low concentrations of nitric oxide in a sample, the method comprising:
   providing an electrode; and
   using the electrode to detect low concentrations of nitric oxide in a sample;
   wherein the electrode comprises:
      a core made from a material selected from the group consisting of carbon, platinum, gold, and combinations thereof;
      a surface coating consisting of ruthenium oxide nanoparticles upon the core; and
      a second coating upon the surface coating, the second coating comprising poly(ethylenedioxythiophene).

6. The method of claim 5, wherein the electrode is capable of detecting picomolar concentrations of nitric oxide.

* * * * *